(12) United States Patent
Xi et al.

(10) Patent No.: US 7,973,010 B2
(45) Date of Patent: Jul. 5, 2011

(54) FULL LENGTH POLYNUCLEOTIDE CODING CHICKEN TYPE II COLLAGEN AND THE USE OF IT

(75) Inventors: Yongzhi Xi, Beijing (CN); Caixia Xi, Beijing (CN)

(73) Assignee: Affiliated Hospital of Academy of Military Medical Sciences, PLA, Beijing (CN)

( * ) Notice: Subject to any disclaimer, the term of this patent is extended or adjusted under 35 U.S.C. 154(b) by 0 days.

(21) Appl. No.: 10/534,538

(22) PCT Filed: Nov. 14, 2003

(86) PCT No.: PCT/CN03/00967
§ 371 (c)(1),
(2), (4) Date: Oct. 31, 2005

(87) PCT Pub. No.: WO2004/052910
PCT Pub. Date: Jun. 24, 2004

(65) Prior Publication Data
US 2006/0276383 A1    Dec. 7, 2006

(30) Foreign Application Priority Data

Nov. 14, 2002  (CN) .................................. 02 1 49375

(51) Int. Cl.
*A61K 38/39*  (2006.01)
*C07K 14/78*  (2006.01)
*C07H 21/04*  (2006.01)
*C12P 21/06*  (2006.01)
*C12N 5/06*  (2006.01)

(52) U.S. Cl. ...... 514/12; 435/69.1; 435/349; 435/320.1; 530/356; 536/23.5

(58) Field of Classification Search ........................ None
See application file for complete search history.

(56) References Cited

U.S. PATENT DOCUMENTS 6,010,722 A *  1/2000  Matsumoto et al. .......... 424/548
6,323,319 B1  11/2001  Alkayali

FOREIGN PATENT DOCUMENTS

WO         02/058484        8/2002

OTHER PUBLICATIONS

Eck et al. (Phar Basis Ther 1995; 77-101).*
Verma et al (Nat. Sep. 1997; 389:239-242).*
Upholt et al. (PNAS. Apr. 1986; vol. 83: 2325-2329).*
Chicken Collagen II amino acid sequence. accession No. AAK98621.*
Protein alignment—chicken COL2A1 and SEQ1-translations.*
DNA alignment—chicken COL2A1 cDNA and SEQ1.*
DNA alignment—chicken COL2A1 cDNA and SEQ2.*
Vuorio et al. (Nucleic Acids Research. 1982; 10:1175-1192).*
Sandell et al. (Journal of Biological Chemistry. 1984; 259(12): 7826-7834).*
Sandell et al. (Journal of Biological Chemistry. 1983; 258(19): 11617-11621).*
Young et al. (Nucleic Acids Res. 1984; 12 (10), 4207-4228).*
Chicken collagen, type 2A1, complete coding sequence.*
MEMO—sequence interpretation.*
GenBank—chicken collagen 2a—mRNA references (2011).*
X. Caixia, et al., "Gallus Gallus Alpha 1 Type IIA Collagen Precursor (COL2A1) mRNA, Complete cds, Alternatively Spliced", EBI Database Accession No. AY046949, XP002529706, Sep. 11, 2001, 3 pages.
Linda J. Sandell, et al., "Structure and Sequence of the Chicken Type II Procollagen Gene, Characterization of the Region Encoding the Carboxyl-Terminal Telopeptide and Propeptide", The Journal of Biological Chemistry, The American Society of Biological Chemists, vol. 259. No. 12, XP000615863, Jun. 25, 1984, pp. 7826-7834.
Linda J. Sandell, et al., "Identification of Genomic DNA Coding for Chicken Type II", The Journal of Biological Chemistry, vol. 258. No. 19, XP002529704, Apr. 4, 1983, pp. 11617-11621.
Hyun-Duck Nah, et al., "Type II Collagen mRNA Containing an Alternatively Spliced Exon Predominates in the Chick Limb Prior to Chondrogenesis", The Journal of Biological Chemistry, The American Society for Biochemistry and Molecular Biology, vol. 266, No. 34, XP002529705, May 15, 1991, pp. 23446-23452.
X. Caixia, et al., "Alpha 1 Type IIA Collagen COL2A1 from Gallus Gallus", EBI Database Accession No. Q90W37, XP002529770, Dec. 1, 2001, 1 page.
David E. Trentham, et al., "Effects of Oral Administration of Type II Collagen on Rheumatoid Arthritis", Science, vol. 261, No. 5129, XP002529769, Sep. 24, 1993, pp. 1727-1730.

* cited by examiner

*Primary Examiner* — Scott Long
(74) *Attorney, Agent, or Firm* — Oblon, Spivak, McClelland, Maier & Neustadt, L.L.P.

(57) ABSTRACT

The present invention relates to a nucleic acid molecule as set forth in SEQ ID NO:1 comprising a polynucleotide sequence encoding full length chicken type II collagen (CCII), or a fragment thereof in possession of the same biological functions as well as CCII encoded thereof. It also relates to a method for producing CCII, and its use in the manufacture of a medicament for treating and/or preventing rheumatoid arthritis (RA). The invention specifically relates to a pharmaceutical composition for treating and/or preventing osteoarthritis and RA, to a food or beverage composition, and to a food additive composition, containing CCII prepared according to the method described in this invention, and the use of the nucleic acid molecules of the present application in gene therapy.

4 Claims, 7 Drawing Sheets

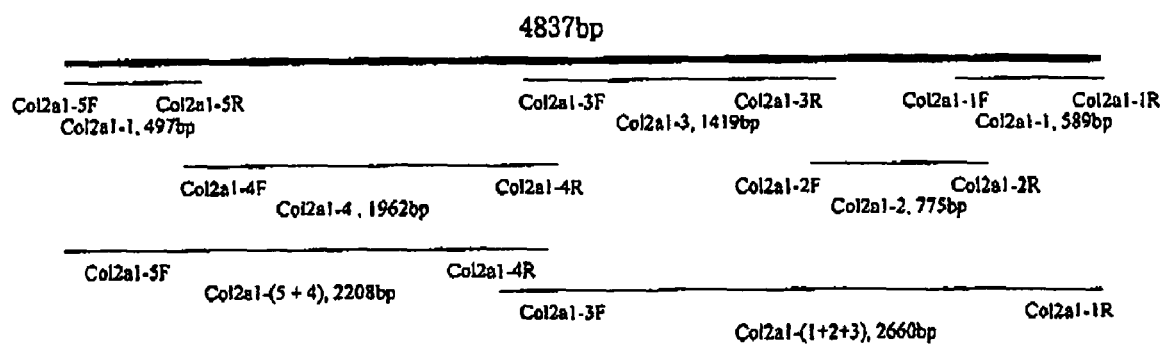
Fig 1. PCR cloning strategy for the genes encoding full length CCII

COL2A1 cDNA corresponding to protein structure

Signal peptide | N-Propeptide

MHGRRPPRSAALLLLLLLLLTAAAAA | QDRDLRQPGPKGQKGEPGDIKDVVGPRGPPGPQGPAGEQGQRGDRGEKGEKGAPGPRGRDGEPGTPGNPGPPGPPGPPGPPGLGGN

FAA QMAGGFDEKAGGAQMGVMQ GPMGPMGPRGPPGPTGAPGPQG

N-Telopeptide     Helical domain

PQGNPGEPGEPGAAGPMGPR GPPGPPGKPGDDGETGKPGKSGERGPPGPQGARGFPGTPGLPGVKGHRGYPGLDGAKG

EAGAPGAKGESGSPGENGSPGPMGPRGLPGERGRPGPSGAAGARGNDGLPGPAGPPGPVGPAGAPGFPGAPGSKGEAGPTGARGPE

GAQGPRGESGTPGSPGPAGAPGNPGTDGIPGAKGSAGAPGIAGAPGFPGPRGPPGPQGATGPLGPKGQTGEPGIAGFKGEQGPKGE

TGPAGPQGAPGPAGEEGKRGARGEPGAAGPVGPPGERGAPGNRGFPGQDGLAGPKGAPGERGPAGLAGPKGATGDPGRPGEPGLPG

ARGLTGRPGDAGPQGKVGPTGAPGEDGRPGPPGPQGARGQPGVMGFPGPKGANGEPGKAGEKGLPGAPGLRGLPGKDGETGAAGPP

GPAGPVGERGEQGAPGPSGFQGLPGPPGPPGESGKPGDQGVPGEAGAPGLVGPRGERGFPGERGSPGAQGLQGPRGLPGTPGTDGP

KGATGPAGPNGAQGPPGLQGMPGERGAAGIAGLKGDRGDVGEKGPEGAPGKDGARGLTGPIGPPGPAGPNGEKGESGPPGPSGAAG

ARGAPGERGEPGAPGPAGFAGPPGADGQPGAKGEQGEPGQKGDAGAPGPQGPSGAPGPQGPTGVTGPKGARGAQGPPGATGFPGAA

GRVGPPGPNGNPGPPGPPGSAGKDGPKGVRGDAGPPGRAGDPGLQGPAGPPGEKGEPGEDGPAGPDGPPGPQGLAGQRGIVGLPGQ

RGERGFPGLPGPSGEPGKQGAPGSAGDRGPPGPVGPPGLTGPAGEPGREGNPGADGLPGRDGAAGVKGDRGETGPVGAPGAPGAPG

APGPVGPTGKQGDRGETGAQGPMGPSGPAGARGMPGPQGPRGDKGETGEAGERGLKGHRGFTGLQGLPGPPGPSGDQGAAGPAGPS

GPRGPPGPV

| C-Telopeptide |

GPSGKDGSNGMPGPIGPPGPRGRS GEPGPAGPPGNPGPPGPPGPP GTGIDMSAFAGLGQTE KGPDPIRYMRA DEA

C-Propeptide

AGGLRQHDVEVDATLKSLNNQIESIRSPEGSKKNPARTCRDIKLCHPEWKSGDYWIDPNQGCTLDAIKVFCNMETGET

CVYPTPSSLPRKNWWTSKTKDKKHVWFAETINGGFHFSYGDENLSPNTASIQMTFLRLLSTEGSQNVTYHCKNSIAYMDEETGNLK

KAILIQGSNDVEIRAEGNSRFTYSVLEDGCTKHTGKWGKTVIEYRLQKTSRLSIVDTAPMDIGGADQEFGVDIGPVCFL

Fig 2: protein structure of chicken type II collegan

Fig 3: Results from RT-PCR of 17-day-old chicken embryo CCOL2A1 3' UTR
1.heart, 2.liver, 3.vitreum, 4.cornea, 5.skin, 6.thymus gland, 7.pectoralis, 8. cornea, 9. small intestine, 10. arthrodial cartilage, 11.spleen, 12. meniscus, 13.skull, 14.testis

Fig.4: Results from RT-PCR of adult chicken CCOL2A1 3' UTR
1.heart, 2.liver, 3.vitreum, 4.cornea, 5.skin, 6.thymus gland, 7.pectoralis, 8. cornea, 9. small intestine, 10. arthrodial cartilage, 11.spleen, 12. meniscus, 13.skull, 14.testis

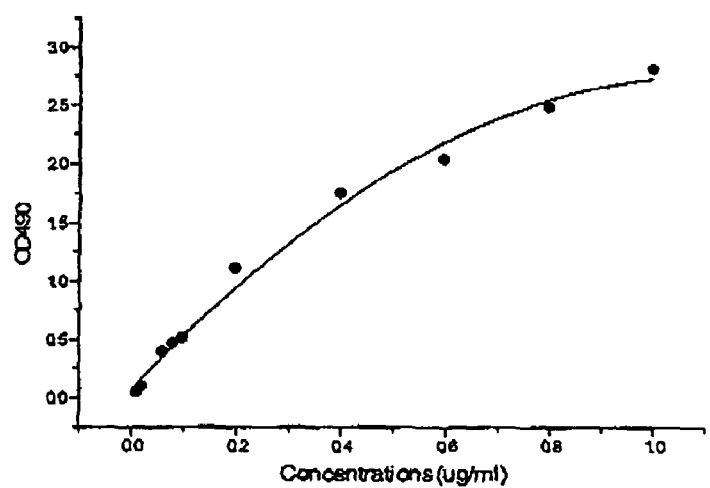

Fig5: standard curve of CCII concentration-absorbance

Fig 6: splicing analysis of COL2A1 exon 2
1. liver, 2.skin, 3. vitreum, 4. small intestine, 5. pectoralis,
6.cornea, 7.articular cartilage, 8.breast bone 9.M
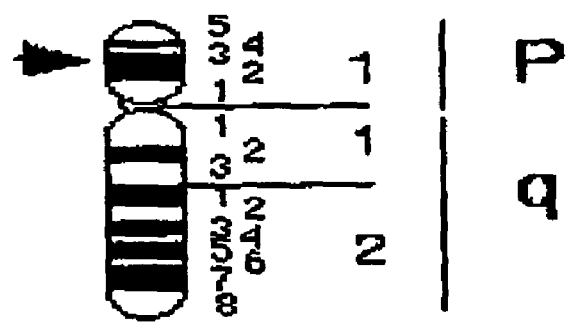
Fig.7: the chromosome band of the genes encoding CCII
Fig 8.division phase of the chicken chromosome

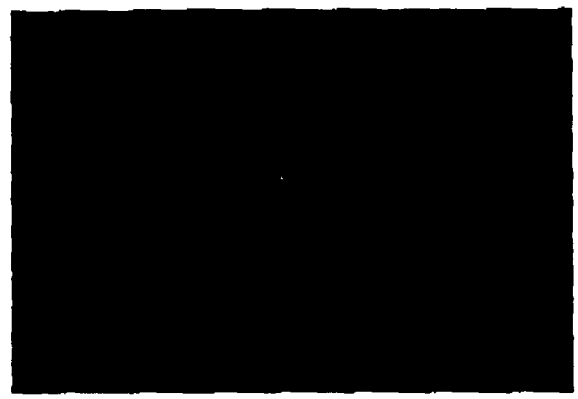
Fig 9  results of ISH hybridization
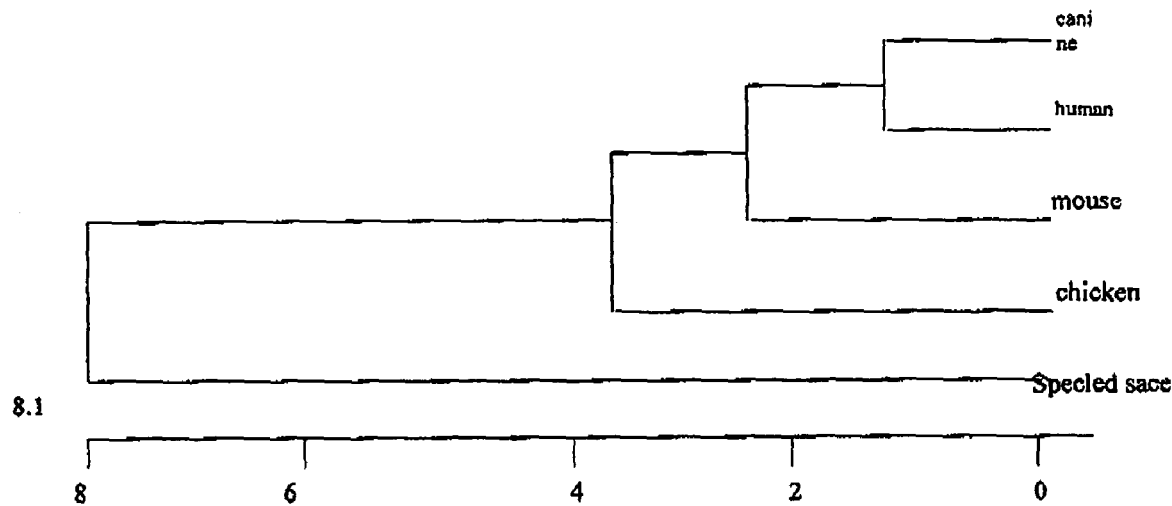
Fig.10: homologous comparison of the evolutionary tree between human being, dog, mouse, chicken and speckled dace

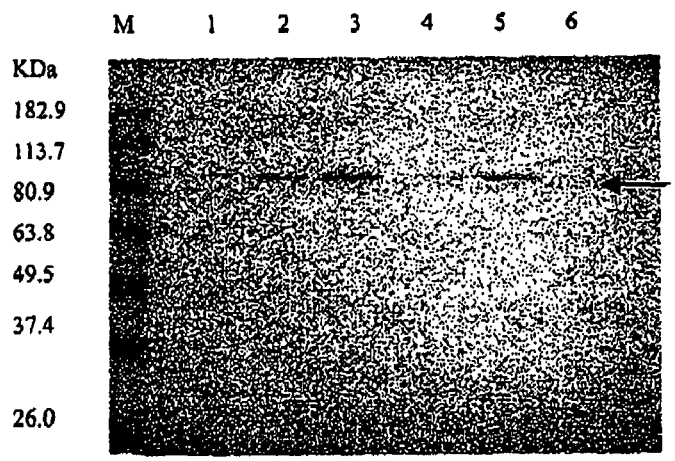
Fig. 11(A). Western blot analysis of pPIC9K/CCOL2A1 cytolysates. M: Lanes 1-5: bands for the induced cell lysis of pPIC9K/CCOL2A1. Lane 6: negative control transformed with vector DNA only. Protein molecular weight standard is shown at left (M).
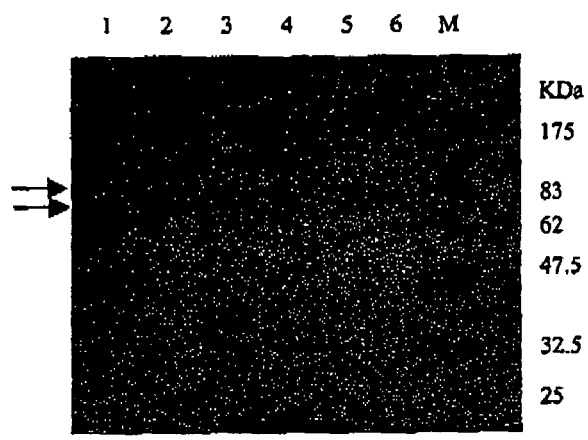
Fig 11(B). pPICZαB/CCOL2A1 cytolysate Western blot results. Protein molecular weight standard is shown at right (M).

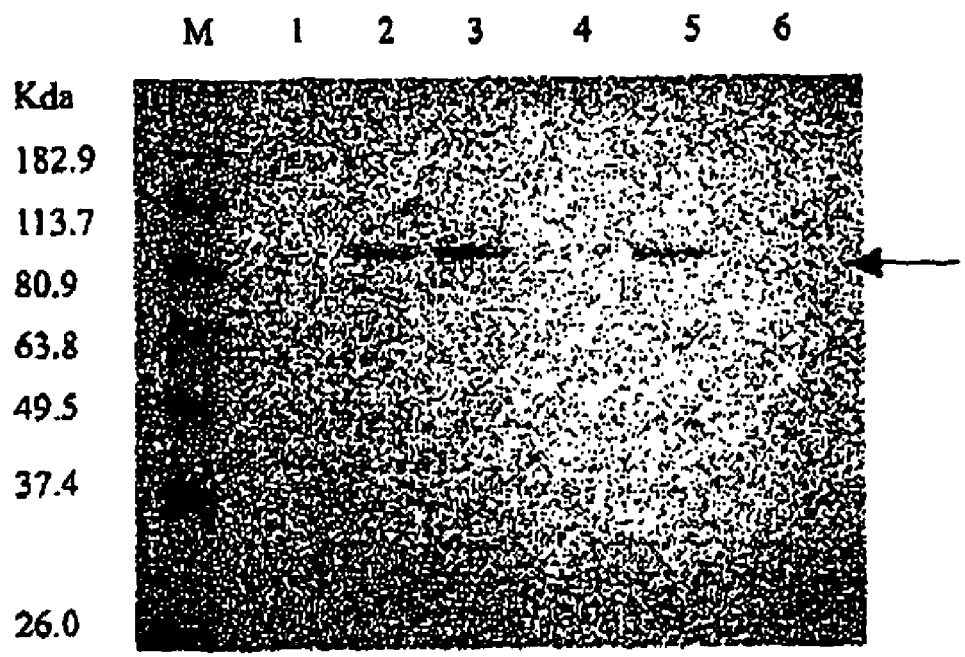
Fig. 12. Western blot analysis of the cell lysis CCOL2A1 produced by pPICZαB/CCOL2A1 co-expression with pPIC9K/P4Hα and pPIC9/P4H β
Lanes 1-5: positive bands for the induced cell lysis of CCOL2A1
Lane 6: negative control tranformed with vector DNA only ID NO:1 comprising a polynucleotide

SEQUENCE LISTING

<160> NUMBER OF SEQ ID NOS: 29

<210> SEQ ID NO 1
<211> LENGTH: 5495

```
<212> TYPE: DNA
<213> ORGANISM: Gallus gallus

<400> SEQUENCE: 1
ccaggcaagg atggcgcacg tgtaagtggg gcacggccat ggggtgggct ggcaaaggat      60
gctcacagag accacatcct catctctctc tctctcccat agggtctgac gggtcccatt     120
ggtccccctg ccctgctgg ccccaacggt gagaaggtga gagcagcatc acagcacccc     180
acattacgcc ccatgggatg accccagtgc ctccacctct ccatcctttc ttttccaggg     240
tgaatccggc cctcctggtc catctggtgc tgccggtgcc cgtggtgccc cgtaagcac      300 aatgtctgca gcccctgggt gcccctaacc ttcaccctaa acccccatca acccctttat     360
caacctcccc catctcttcc cattagggtg agcgtggcga gcccggtgcc cccggtcctg     420
ctggatttgc tggccccccg gtgagtgttt caccccgaag cccccatcgc acacccacgt     480
cttcacccca catcctcacc ccactcatgg tggctgctgt cccatcagg gcgccgatgg     540 acaacccggt gccaaaggcg agcagggaga gcccgggcag aagggtgacg cgggcgctcc     600
tggtccccaa ggtccctccg gcgctcctgg cccccaggta caacaccaaa tggggcaaac     660
ccccaaattt gggacgtcac ggccccaatg caggcacact gcagctcccg ttcggatttg     720
taacctgttt ttctctcctt cctagggtcc aaccggtgtc actggtccca aaggagctcg     780
tggggctcag ggtccccctg tgagtaccgg ggggtgggct gcagggtggg gaaggagcgg     840
ccgtggggct gagctgtgtc tgagccgttt ctcctctccc tctctcctct gactctgtga     900
ttccctcccc agggagccac gggattcccc ggagctgccg gccgtgtggg accgcccggc     960
cctaatgtga gtctgggggc gttctgggat tgcccccacc tggggtttgg gcgctgcttc    1020
cccgcgctgc gtgttggagg gggcactgtt tccctgcaca gacacgtggg gtttcctcc    1080 ttggctctct gatgttggct tttggggcca ttccaatggt agagaaggac ttttctaagg    1140
gcaagagctc cccaagaagc agcagtggga tgcgggtgat aaagatggaa tggctgcctc    1200
tggtttgcac caacgctgct ttccttccct ttagggtaac ccaggccccc ccggaccccc    1260
cggctctgct ggcaaagacg gccccaaggg tgttcgtggc gacgccggcc cccccggccg    1320
tgcaggtgac cccggcctcc aaggccccgc cggccccccc ggcgagaagg gcgaacccgg    1380
cgaggacggc cccgcggtga ggattctggg ggtctcctcc ctccgtgcac cccctggctg    1440
cgtggtgccg ttgttcttag tctgatttcc ccctctgctg ccctgcaggg tcccgacggc    1500
cccccccggc cctcaaggct tggcaggaca gcgtggtatt gtgggtctcc caggacagcg    1560
tggtgagaga ggcttccccg gactgccggg gccatcggtg agtgggtcgc tctcatttgg    1620
gtgcactgaa tcctatgggg tgcagagatg tggggccgc gatgctctgg agcccatctc    1680
aggggtcgcc agccctttgg tgcagcccgg ggacaccgtt tgcaggtggg ttggggtttt    1740
gcggagctcc ttttcccca ccaggagccg ctggtgcaag gcttaaagcc ggggcaggaa    1800
aaccatcagt ggttatttgt tgcagagggg tctgggagcc ataaaaaacg gggaaggggc    1860
agcgctgggg tctctcccac tcatgcacct ctttcccatc tttcagggag aacctggaaa    1920
gcaaggagcg cctggctctg cgggtgaccg aggtcccccc ggccccgtgg gccccctgg    1980 gctgacaggt cctgctggag aacccggccg cgaggtaagc aaaaccccac agcatcacag    2040
cggcaccggg catcaccaac cccatggcac agctcagctc ccagagctcc ccggtgtctt    2100
tttctccagc actgaaagga gactttgcac aaatcctgct ccacccgggt tgtaacatcc    2160
ccttttcctc ctagggcaac cctggtgctg acgtcccccc aggcagggat ggcgcagctg    2220
gcgtgaaggt gagcttgcca tgcgctcccc attggcactc gccatccccg tgccaaaagc    2280
```

```
tgtggggttt tgcacagatc tgacctctct gttgtctgct cgcagggtga tcgtggtgag    2340
accggccctg tgggtgctcc cggtgctcct ggagcccctg gcgccccgg  ccctgttggt    2400 cccactggaa aacaaggaga cagaggcgag acggtgagtg ctggcacaag ggtttagggt    2460
ttagggtctc cttatggctg aaaatgtgca ggggttcccc tcaaggtttg ttccttgcac    2520
cagtgctgag tgcatttaaa gatgctgtga ggcaccaaca gctgctgatt gtcactgttg    2580
cccggatctg gggtgcggag catggggctg gctcagacac ccccgaaatc ccaaattcat    2640
ggcttcgagg tggtgcttct ggtcgctggc accttctgat gtccttttt  tctccctgca    2700 gggtgcacaa gggcccatgg gtccctctgg tcccgctgga gctcgaggaa tgccggtgag    2760
tggtgctgag tgcatcggca catcccacgt acagagcgtg gggtcctgcg tgccaggagg    2820
gggtctgcca ccctgagccc gacacagccc tgtccccact ttagggtccc caaggacctc    2880
gtggtgacaa aggtgagacg ggagaggctg gagagagagg gctgaagggc caccgcggct    2940
tcaccggtct gcagggtctg cccggaccac ccgtaagttg gtttgggag  cactgagccc    3000 ccccccccgt acgatgcggc tcctttgggg tctctgtggc caccgaggct ctgtctggcc    3060
caaagtgctg accgcagagc tgtgaccacc ccggcttcct cctcagggcc cgtctggaga    3120
ccaaggtgct gccggtcccg ctggtccctc cggtcccaga gtaagtcctg acggtggtgt    3180
ttggggtggt ggaaggggaa ggagcagcag tggcctccct gggcacctgc agcctctgtt    3240
cgctcctgtc tgctcatcag caccatcgcc ttccctgccc tgaggcccg  caatgccttc    3300 acctcccccgt tttggggctc tctcctaggg tcccctggt  cccgtcggcc cctctggcaa    3360
agacggctct aacggcatgc ccggccccat cggtcctccc ggtcccgtg  acggagtgg    3420 tgaacccggc cctgcggtga gtcctggtga ggggaggcag ggaatggggt ccagctcgca    3480
gagcagccca tcagcatcac ttcttcc   cataggtcc tcctggaaac cccggtcctc    3540
ccggtcctcc tggcccccccc ggcaccggca tcgacatgtc tgcttttgct ggactgggtc    3600
agacggagaa gggccccgac ccatccgct  acatgggggc agacgaggcg gccggagggc    3660
tgcggcagca cgacgtggag gtggacgcca ccctcaaatc cctcaacaat cagattgaga    3720
gcatccgcag ccccgagggc tccaagaaga acctgccag  gacctgccgc gacatcaaac    3780
tctgccatcc cgagtggaag agcggtaaga gctccgcgtg cctctcccgt cctccctct    3840 tccccacagg agagcatccc cagcgtcctc gcaccgacct gcggtcaggt tggatgttag    3900
gaaagattcc ttgtccaaaa gagctctggg cgctgggctg gctgccgg   ggaggtgggg    3960 cagtcgctgt ccccataggt gttggggaac tgtggagatg tggcacttgg gagcgtggct    4020
tagtggggat gaggcagcag ttggaccaat cttcgaggtc ttctccagtc ttaatggctc    4080
tgtgcttctg tcggtgtgca tggtggtgat gggtggccat ttagacttgg cgatctttga    4140
ggtcttttcc gatcttaacg actcctagac ctccccaacc ccatgaacgc tgtttgtcct    4200
cccccctgca ggagattact ggattgaccc gaaccagggc tgcaccttgg acgccatcaa    4260
agtattctgc aacatggaga caggcgagac ctgcgtctac ccgaccccca gcagcatccc    4320
caggaagaac tggtggacca gcaagacgaa agacaagaag cacgtctggt ttgcagagac    4380
catcaacggc ggtttccacg tgggtgtccc ccgggtgtcc ttggaaggat cgatcccacc    4440
tgggatgtcc ttcttgcggt catgtggatg ggttttaatg aagttataga gggtgattct    4500
gaaggtgtag gtttgggtca gttcagctcc acaaatcaaa gggaaaggat gggatggagc    4560
aactgagctc cctcggtttg tttgcccag  aaaaggtgag gatgagggga ggcctcacgg    4620
ccctacagcc ccttacggcc ctacagcagc gttaggaaaa aagttctgcc ccggagctgt    4680
```

```
gttgggcaca gaacagccct gtgatgccgg agctcgggga gcattgggac aacgctctca    4740
gacattgggt ttgggtcagg tcctgggtaa cgtgatgtgc aggggcaac cagcccatgg     4800 gtgggcttta aggacccttc caagccaacc attccatggt tctgtgatct gtaaggacct    4860
ttccaatcca aaccactctg attttttct cagccatttg ggaacctgaa gtacggaagt     4920
cctcccaaaa agctcctgag agtaaggtgg tcataatgcc cgcaggcttt aactcctcac    4980
ctcttccctc cagttcagct acggcgatga gaacctgtcc cccaacaccg ccagcatcca    5040
gatgaccttc ctgcgcctcc tgtccaccga gggctcccag aacgtcacct accactgcaa    5100
gaacagcatc gcctacatgg acgaggagac gggcaacctg aagaaagcca tcctcatcca    5160
gggatccaac gacgtggaga tcagagccga gggcaacagc aggttcacct acagcgtctt    5220
ggaggacggc tgcacggtag gttgctgggc gcctgcaaag gaaaggtgca gatggggagg    5280
gggaggctga ggctgggggg atgaggccga agcagctgac agcatccctg ccctccttcc    5340
ctccccagaa acacactggc aaatgggca agacggtgat cgagtaccgg tcgcagaaga    5400
cctcgcgcct gcccattgta gatattgcac ctatggacat tggcggagcc gatcaggagt    5460
ttggcgtgga tattggccca gtctgcttct tgtaa                               5495

<210> SEQ ID NO 2
<211> LENGTH: 4793
<212> TYPE: DNA
<213> ORGANISM: Gallus gallus

<400> SEQUENCE: 2
atgcacggcc gccgcccgcc ccgctccgcc gctctcctcc tcctcctcct ccttctcacg    60
gccgccgcaa ccgcgcagga ccgcgacctc cgacaacctg ccccaaggg acagaaggga     120 gaacccggag atattaaaga tgttgtagga ccccgagggc ctccaggacc cagggccca    180 gcaggagagc agggacagcg agggaccgt ggcgagaagg gggagaaggg tgctcctggc     240
ccccgtggga gggatggaga acccggcacc cctggaaacc caggcccccc cggtcccccc    300
ggacctcctg gcccccccgg acttggtgga aactttgcgg cgcagatggc gggcggcttc    360
gatgagaagg cgggtggagc gcagatgggt gtcatgcagg gacccatggg ccctatggga    420
ccccgcggcc cccctggccc cactggcgca cctggtcccc agggatttca aggcaacccc    480
ggtgagcccg gcgaacccgg cgctgctggt ccgatgggtc cccggggacc tccgggacca    540
cctgggaaac ccggtgacga tgtgagaca ggcaaacccg gcaaatctgg tgaacgtggc     600 cccccccggcc cccagggcgc tcgtggcttc cctgggactc ctggtctccc cggagtgaag    660
ggccaccgag gctaccccgg tttggatggt gccaaaggag aggcgggggc tcctggagcc    720
aagggtgaat ctggttcacc gggtgagaac ggctcccccg gccccatggg accccgtggg    780
ctgcccggag agcgaggacg tcccggcccc tccggcgccg ccggtgctcg tggcaatgac    840
ggtctccctg gcctgctgg accccctgga cccgtcggcc ctgccggagc cccggcttc     900 cccggagccc ccggttcaaa gggtgaagcc ggcccactg gtgcacgggg tcccgagggt     960
gcccaaggac cccgcggcga atccggcacc cccggctctc ccggccccgc tggcgcaccc    1020
ggtaacccag ggactgatgg catccccggt gccaagggct cggcgggtgc cccgggcatt    1080
gcaggcgctc caggattccc cggccacgc ggcccccccg accccaagg tgccaccgga     1140 ccactgggac ccaaaggaca gacgggcgaa cccggcatcg caggcttcaa gggcgagcaa    1200
ggaccgaagg gcgagacggg ccccgcagga ccccaaggtg ccccggggcc ggctggtgag    1260
gaaggcaaga gaggagctcg tggtgaacct ggtgccgccg gccctgtggg cccccccgga    1320
```

```
gaaaggggcg ctcctggcaa ccgtggattc cccgggcagg acgggctggc cggacccaag    1380
ggtgctccag gtgaacgcgg ccccgctggt ctcgccggtc ccaaaggtgc caccggtgac    1440
cccggacgtc ccggagagcc cgggctgccc ggagcgaggg gtctcaccgg ccgcccggc     1500 gatgcgggac ctcaaggcaa agtcggccca actggtgctc ctggcgagga tggccgcccc    1560
ggcccccccg gacctcaggg tgctcgtggg cagcctggtg tgatgggttt ccccggtccc    1620 aaggcgcta atggtgagcc tggaaaagct ggagagaaag gactgccgg cgccccaggg     1680 ctgcggggtc tgcctggcaa ggatggggag acgggagctg ccggcccccc tggacccgct    1740
ggtcctgtgg gtgagagagg agagcaagga gccccggtc cttccggctt ccagggactg     1800
cccggaccac caggtccccc tggggagagc ggcaaaccc gagaccaggg tgttcctgga    1860
gaagccggtg cccccggtct tgttggtccc agaggtgaac gtggattccc cggtgaacgc    1920
ggctctcccg gtgcccaagg gctgcagggt cccgtgggc tccccggaac gcccggcact     1980 gacgaccca agggtgcaac cggtccagcc ggccccaacg gtgcccaggg tcccccaggg    2040
ctgcagggaa tgcccggtga gagaggagca gctggcatcg ctggcctcaa gggtgaccgg    2100
ggagatgttg tgagaaagg acctgaggga gctccaggca aggatggcgc acgtggtctg    2160
acgggtccca ttggtccccc tggccctgct ggccccaacg gtgagaaggg tgaatccggc    2220
cctcctggtc catctggtgc tgccggtgcc cgtggtgccc ccgtgagcg tggcgagccc    2280 ggtgccccg gtcctgctgg atttgctggc ccccgggcg ccgatggaca cccggtgcc     2340 aaaggcgagc agggagagcc cgggcagaag ggtgacgcgg gcgctcctgg tccccaaggt    2400
ccctccggcg ctcctggccc cagggcca accggtgtca ctggtcccaa aggagctcgt     2460
ggggctcagg gtccccctgg agccacggga ttccccggag ctgccggccg tgtgggaccg    2520
cccggcccta atggtaaccc aggccccccc ggaccccctg gctctgctgg caaggacggc    2580
cccaagggtg ttcgtggcga cgccggcccc ccggccgtg caggtgaccc cggcctccaa    2640
ggccccgccg gccccccgg cgagaagggc gaacccggcg aggacggccc cgcgggtccc    2700 gacgccccc ccgccctca aggcttggca ggacagcgtg gtattgtggg tctcccagga    2760
cagcgtggtg agagaggctt cccggactg ccggggccat cgggagaacc tggaaagcaa    2820
ggagcgcctg gctctgcggg tgaccgaggt ccccccggcc ccgtgggcc ccctgggctg    2880 acgggtcctg ctggagaacc cggcgcgag gcaaccctg gtgctgacgg tctcccaggc    2940
agggatggcg cagctggcgt gaaggtgat cgtggtgaga ccggccctgt gggtgccccc    3000
ggtgctcctg gagcccctgg cgccccggc cctgttggtc ccactggaaa acaaggagac    3060
agaggcgaga cgggtgcaca agggcccatg ggtccctctg gtcccgctgg agctcgagga    3120
atgccgggtc cccaaggacc tcgtggtgac aaaggtgaga cggagaggc tggagagaga    3180 gggctgaagg gccaccgtgg cttcaccggt ctgcagggtc tgccggacc acccggcccg    3240 tctggagacc aaggtgctgc cggtcccgct ggtccctccg gtcccagagg tccccctggt    3300
cccgtcggcc cctctggcaa agatggctct aacggcatgc ccggcccat cggtcctccc    3360 ggtccccgtg gacggagtgg tgaacccggc cctgcgggtc ctcctggaaa ccccggtcct    3420
cccggtcctc ctggccccc cggcaccggc atcgacatgt ctgcttttgc tggactgggt    3480
cagacgagaa agggccccga ccccatccgc tacatgaggg cagacgaggc ggccggaggg    3540
ctgcggcagc acgacgtgga ggtggatgcc accctcaaat ccctcaacaa tcagattgag    3600
agcatccgca gccccgaggg ctccaagaag aaccctgcca ggacctgccg cgacatcaaa    3660
ctctgccatc ccgagtggaa gagcggagat tactggattg acccgaacca gggctgcacc    3720
```

```
ttggacgcca tcaaagtatt ctgcaacatg gagacgggcg agacctgcgt ctacccgacc    3780
cccagcagca tccccaggaa gaactggtgg accagcaaga cgaaagacaa gaagcacgtc    3840
tggtttgcag agaccatcaa cggcggtttc cacttcagct acggcgatga gaacctgtcc    3900
cccaacaccg ccagcatcca gatgaccttc ctgcgcctcc tgtccaccga gggctcccag    3960
aacgtcacct accactgcaa gaacagcatc gcctacatgg acgaggagac gggcaacctg    4020
aagaaagcca tcctcatcca gggatccaac gacgtggaga tcagagccga gggcaacagc    4080
aggttcacct acagcgtctt ggaggacggc tgcacgaaac acactggcaa atggggcaag    4140
acggtgatcg agtaccggtt gcagaagacc tcgcgcctgt ccattgtaga tactgcacct    4200
atggacattg gcggagccga tcaggagttt ggcgtggata ttggcccagt ctgcttcttg    4260
taaaaagggt tgttgttatt tgtgtgtttg tttgttgttt ggttgttgtt ttttgtttct    4320
tttttttttt ttttagaaa agaaaggaat ccagcccaat cccataaaag caaaccagtc    4380 ccaccccccag gacccgcacg ttcccagcac aacttctgca ctgaacggat ggcacgaccc    4440 cgcgccccctt cgggaccctc cggcgccgtc accgggcaga ctgcgaaata caaccacggg    4500
cttatattta tttattgcct tcctggaagg cctggtttcg tagggcgggt ggaggtggga    4560
atcaatctgg caggtgtgac ggccccccctc cccacaaagg gatctggcaa acgcaggtat    4620
cgcgaatccc ctcccctccc cgtgtatcac cagcaggagt gctaatgtat catacaacag    4680
aaatggtgct attcttgtaa aacaagtctg tatttttaa catcagttga tataaaaaca    4740
acaaaaaaaa aaactttttgg tggaaagtaa aaaaacaaa aaaaaaaaaa aaa           4793
```

<210> SEQ ID NO 3
<211> LENGTH: 1420
<212> TYPE: PRT
<213> ORGANISM: Gallus gallus

<400> SEQUENCE: 3

```
Met His Gly Arg Arg Pro Pro Arg Ser Ala Ala Leu Leu Leu Leu Leu
1               5                   10                  15

Leu Leu Leu Thr Ala Ala Ala Ala Ala Gln Asp Arg Asp Leu Arg Gln
            20                  25                  30

Pro Gly Pro Lys Gly Gln Lys Gly Glu Pro Gly Asp Ile Lys Asp Val
        35                  40                  45

Val Gly Pro Arg Gly Pro Pro Gly Pro Gln Gly Pro Ala Gly Glu Gln
    50                  55                  60

Gly Gln Arg Gly Asp Arg Gly Glu Lys Gly Lys Gly Ala Pro Gly
65                  70                  75                  80

Pro Arg Gly Arg Asp Gly Glu Pro Gly Thr Pro Gly Asn Pro Gly Pro
                85                  90                  95

Pro Gly Pro Pro Gly Pro Pro Gly Pro Pro Gly Leu Gly Gly Asn Phe
            100                 105                 110

Ala Ala Gln Met Ala Gly Gly Phe Asp Glu Lys Ala Gly Gly Ala Gln
        115                 120                 125

Met Gly Val Met Gln Gly Pro Met Gly Pro Met Gly Pro Arg Gly Pro
    130                 135                 140

Pro Gly Pro Thr Gly Ala Pro Gly Pro Gln Gly Phe Gln Gly Asn Pro
145                 150                 155                 160

Gly Glu Pro Gly Glu Pro Gly Ala Ala Gly Pro Met Gly Pro Arg Gly
                165                 170                 175

Pro Pro Gly Pro Pro Gly Lys Pro Gly Asp Asp Gly Glu Thr Gly Lys
            180                 185                 190
```

Pro Gly Lys Ser Gly Glu Arg Gly Pro Pro Gly Pro Gln Gly Ala Arg
            195                 200                 205

Gly Phe Pro Gly Thr Pro Gly Leu Pro Gly Val Lys Gly His Arg Gly
        210                 215                 220

Tyr Pro Gly Leu Asp Gly Ala Lys Gly Glu Ala Gly Ala Pro Gly Ala
225                 230                 235                 240

Lys Gly Glu Ser Gly Ser Pro Gly Glu Asn Gly Ser Pro Gly Pro Met
                245                 250                 255

Gly Pro Arg Gly Leu Pro Gly Glu Arg Gly Arg Pro Gly Pro Ser Gly
            260                 265                 270

Ala Ala Gly Ala Arg Gly Asn Asp Gly Leu Pro Gly Pro Ala Gly Pro
        275                 280                 285

Pro Gly Pro Val Gly Pro Ala Gly Ala Pro Gly Phe Pro Gly Ala Pro
            290                 295                 300

Gly Ser Lys Gly Glu Ala Gly Pro Thr Gly Ala Arg Gly Pro Glu Gly
305                 310                 315                 320

Ala Gln Gly Pro Arg Gly Glu Ser Gly Thr Pro Gly Ser Pro Gly Pro
                325                 330                 335

Ala Gly Ala Pro Gly Asn Pro Gly Thr Asp Gly Ile Pro Gly Ala Lys
            340                 345                 350

Gly Ser Ala Gly Ala Pro Gly Ile Ala Gly Ala Pro Gly Phe Pro Gly
        355                 360                 365

Pro Arg Gly Pro Pro Gly Pro Gln Gly Ala Thr Gly Pro Leu Gly Pro
        370                 375                 380

Lys Gly Gln Thr Gly Glu Pro Gly Ile Ala Gly Phe Lys Gly Glu Gln
385                 390                 395                 400

Gly Pro Lys Gly Glu Thr Gly Pro Ala Gly Pro Gln Gly Ala Pro Gly
                405                 410                 415

Pro Ala Gly Glu Glu Gly Lys Arg Gly Ala Arg Gly Glu Pro Gly Ala
            420                 425                 430

Ala Gly Pro Val Gly Pro Pro Gly Glu Arg Gly Ala Pro Gly Asn Arg
        435                 440                 445

Gly Phe Pro Gly Gln Asp Gly Leu Ala Gly Pro Lys Gly Ala Pro Gly
        450                 455                 460

Glu Arg Gly Pro Ala Gly Leu Ala Gly Pro Lys Gly Ala Thr Gly Asp
465                 470                 475                 480

Pro Gly Arg Pro Gly Glu Pro Gly Leu Pro Gly Ala Arg Gly Leu Thr
                485                 490                 495

Gly Arg Pro Gly Asp Ala Gly Pro Gln Gly Lys Val Gly Pro Thr Gly
            500                 505                 510

Ala Pro Gly Glu Asp Gly Arg Pro Gly Pro Pro Gly Pro Gln Gly Ala
        515                 520                 525

Arg Gly Gln Pro Gly Val Met Gly Phe Pro Gly Pro Lys Gly Ala Asn
        530                 535                 540

Gly Glu Pro Gly Lys Ala Gly Glu Lys Gly Leu Pro Gly Ala Pro Gly
545                 550                 555                 560

Leu Arg Gly Leu Pro Gly Lys Asp Gly Glu Thr Gly Ala Ala Gly Pro
                565                 570                 575

Pro Gly Pro Ala Gly Pro Val Gly Glu Arg Gly Glu Gln Gly Ala Pro
            580                 585                 590

Gly Pro Ser Gly Phe Gln Gly Leu Pro Gly Pro Gly Pro Pro Gly
        595                 600                 605

Glu Ser Gly Lys Pro Gly Asp Gln Gly Val Pro Gly Glu Ala Gly Ala

```
                610                 615                 620
Pro Gly Leu Val Gly Pro Arg Gly Glu Arg Gly Phe Pro Gly Glu Arg
625                 630                 635                 640

Gly Ser Pro Gly Ala Gln Gly Leu Gln Gly Pro Arg Gly Leu Pro Gly
                645                 650                 655

Thr Pro Gly Thr Asp Gly Pro Lys Gly Ala Thr Gly Pro Ala Gly Pro
                660                 665                 670

Asn Gly Ala Gln Gly Pro Pro Gly Leu Gln Gly Met Pro Gly Glu Arg
                675                 680                 685

Gly Ala Ala Gly Ile Ala Gly Leu Lys Gly Asp Arg Gly Asp Val Gly
                690                 695                 700

Glu Lys Gly Pro Glu Gly Ala Pro Gly Lys Asp Gly Ala Arg Gly Leu
705                 710                 715                 720

Thr Gly Pro Ile Gly Pro Pro Gly Pro Ala Gly Pro Asn Gly Glu Lys
                725                 730                 735

Gly Glu Ser Gly Pro Pro Gly Ser Gly Ala Ala Gly Ala Arg Gly
                740                 745                 750

Ala Pro Gly Glu Arg Gly Glu Pro Gly Ala Pro Gly Pro Ala Gly Phe
                755                 760                 765

Ala Gly Pro Pro Gly Ala Asp Gly Gln Pro Gly Ala Lys Gly Glu Gln
                770                 775                 780

Gly Glu Pro Gly Gln Lys Gly Asp Ala Gly Ala Pro Gly Pro Gln Gly
785                 790                 795                 800

Pro Ser Gly Ala Pro Gly Pro Gln Gly Pro Thr Gly Val Thr Gly Pro
                805                 810                 815

Lys Gly Ala Arg Gly Ala Gln Gly Pro Pro Gly Ala Thr Gly Phe Pro
                820                 825                 830

Gly Ala Ala Gly Arg Val Gly Pro Pro Gly Pro Asn Gly Asn Pro Gly
                835                 840                 845

Pro Pro Gly Pro Pro Gly Ser Ala Gly Lys Asp Gly Pro Lys Gly Val
                850                 855                 860

Arg Gly Asp Ala Gly Pro Pro Gly Arg Ala Gly Asp Pro Gly Leu Gln
865                 870                 875                 880

Gly Pro Ala Gly Pro Pro Gly Glu Lys Gly Glu Pro Gly Glu Asp Gly
                885                 890                 895

Pro Ala Gly Pro Asp Gly Pro Pro Gly Pro Gln Gly Leu Ala Gly Gln
                900                 905                 910

Arg Gly Ile Val Gly Leu Pro Gly Gln Arg Gly Glu Arg Gly Phe Pro
                915                 920                 925

Gly Leu Pro Gly Pro Ser Gly Glu Pro Gly Lys Gln Gly Ala Pro Gly
                930                 935                 940

Ser Ala Gly Asp Arg Gly Pro Pro Gly Pro Val Gly Pro Pro Gly Leu
945                 950                 955                 960

Thr Gly Pro Ala Gly Glu Pro Gly Arg Glu Gly Asn Pro Gly Ala Asp
                965                 970                 975

Gly Leu Pro Gly Arg Asp Gly Ala Ala Gly Val Lys Gly Asp Arg Gly
                980                 985                 990

Glu Thr Gly Pro Val Gly Ala Pro  Gly Ala Pro Gly Ala  Pro Gly Ala
                995                 1000                1005

Pro Gly Pro Val Gly Pro Thr  Gly Lys Gln Gly Asp  Arg Gly Glu
                1010                1015                1020

Thr Gly Ala Gln Gly Pro Met  Gly Pro Ser Gly Pro  Ala Gly Ala
                1025                1030                1035
```

```
Arg Gly Met Pro Gly Pro Gln Gly Pro Arg Gly Asp Lys Gly Glu
    1040            1045                1050
Thr Gly Glu Ala Gly Glu Arg Gly Leu Lys Gly His Arg Gly Phe
    1055            1060                1065
Thr Gly Leu Gln Gly Leu Pro Gly Pro Pro Gly Pro Ser Gly Asp
    1070            1075                1080
Gln Gly Ala Ala Gly Pro Ala Gly Pro Ser Gly Pro Arg Gly Pro
    1085            1090                1095
Pro Gly Pro Val Gly Pro Ser Gly Lys Asp Gly Ser Asn Gly Met
    1100            1105                1110
Pro Gly Pro Ile Gly Pro Pro Gly Pro Arg Gly Arg Ser Gly Glu
    1115            1120                1125
Pro Gly Pro Ala Gly Pro Pro Gly Asn Pro Gly Pro Pro Gly Pro
    1130            1135                1140
Pro Gly Pro Pro Gly Thr Gly Ile Asp Met Ser Ala Phe Ala Gly
    1145            1150                1155
Leu Gly Gln Thr Glu Lys Gly Pro Asp Pro Ile Arg Tyr Met Arg
    1160            1165                1170
Ala Asp Glu Ala Ala Gly Gly Leu Arg Gln His Asp Val Glu Val
    1175            1180                1185
Asp Ala Thr Leu Lys Ser Leu Asn Asn Gln Ile Glu Ser Ile Arg
    1190            1195                1200
Ser Pro Glu Gly Ser Lys Lys Asn Pro Ala Arg Thr Cys Arg Asp
    1205            1210                1215
Ile Lys Leu Cys His Pro Glu Trp Lys Ser Gly Asp Tyr Trp Ile
    1220            1225                1230
Asp Pro Asn Gln Gly Cys Thr Leu Asp Ala Ile Lys Val Phe Cys
    1235            1240                1245
Asn Met Glu Thr Gly Glu Thr Cys Val Tyr Pro Thr Pro Ser Ser
    1250            1255                1260
Ile Pro Arg Lys Asn Trp Trp Thr Ser Lys Thr Lys Asp Lys Lys
    1265            1270                1275
His Val Trp Phe Ala Glu Thr Ile Asn Gly Gly Phe His Phe Ser
    1280            1285                1290
Tyr Gly Asp Glu Asn Leu Ser Pro Asn Thr Ala Ser Ile Gln Met
    1295            1300                1305
Thr Phe Leu Arg Leu Leu Ser Thr Glu Gly Ser Gln Asn Val Thr
    1310            1315                1320
Tyr His Cys Lys Asn Ser Ile Ala Tyr Met Asp Glu Glu Thr Gly
    1325            1330                1335
Asn Leu Lys Lys Ala Ile Leu Ile Gln Gly Ser Asn Asp Val Glu
    1340            1345                1350
Ile Arg Ala Glu Gly Asn Ser Arg Phe Thr Tyr Ser Val Leu Glu
    1355            1360                1365
Asp Gly Cys Thr Lys His Thr Gly Lys Trp Gly Lys Thr Val Ile
    1370            1375                1380
Glu Tyr Arg Leu Gln Lys Thr Ser Arg Leu Ser Ile Val Asp Thr
    1385            1390                1395
Ala Pro Met Asp Ile Gly Gly Ala Asp Gln Glu Phe Gly Val Asp
    1400            1405                1410
Ile Gly Pro Val Cys Phe Leu
    1415            1420

<210> SEQ ID NO 4
```

```
<211> LENGTH: 21
<212> TYPE: DNA
<213> ORGANISM: Artificial Sequence
<220> FEATURE:
<223> OTHER INFORMATION: Synthetic DNA

<400> SEQUENCE: 4
tctatcgcgc acccgttgtg c                                              21

<210> SEQ ID NO 5
<211> LENGTH: 22
<212> TYPE: DNA
<213> ORGANISM: Artificial Sequence
<220> FEATURE:
<223> OTHER INFORMATION: Synthetic DNA

<400> SEQUENCE: 5
gtcttgtagt gctacggctt gc                                             22

<210> SEQ ID NO 6
<211> LENGTH: 22
<212> TYPE: DNA
<213> ORGANISM: Artificial Sequence
<220> FEATURE:
<223> OTHER INFORMATION: Synthetic DNA

<400> SEQUENCE: 6
ttgcagatgt ctccaatacc ag                                             22

<210> SEQ ID NO 7
<211> LENGTH: 28
<212> TYPE: DNA
<213> ORGANISM: Artificial Sequence
<220> FEATURE:
<223> OTHER INFORMATION: Synthetic DNA

<400> SEQUENCE: 7
gcacaacggc tcgggcaatg tgctaacg                                       28

<210> SEQ ID NO 8
<211> LENGTH: 20
<212> TYPE: DNA
<213> ORGANISM: Artificial Sequence
<220> FEATURE:
<223> OTHER INFORMATION: Synthetic DNA

<400> SEQUENCE: 8
gctcggaagc aacggcctcg                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic DNA

<400> SEQUENCE: 9
ctcgtcaagc aacggcctcg                                                20

<210> SEQ ID NO 10
<211> LENGTH: 19
<212> TYPE: DNA
<213> ORGANISM: Artificial Sequence
<220> FEATURE:
<223> OTHER INFORMATION: Synthetic DNA

<400> SEQUENCE: 10
```

```
cgctgcgatc gtcatgcgg                                                      19

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA

<400> SEQUENCE: 11
gtagtgaccc tacgcccgag                                                     20

<210> SEQ ID NO 12
<211> LENGTH: 28
<212> TYPE: DNA
<213> ORGANISM: Artificial Sequence
<220> FEATURE:
<223> OTHER INFORMATION: Synthetic DNA

<400> SEQUENCE: 12
acgccggctc tcgtgctcct cgtggtgc                                            28

<210> SEQ ID NO 13
<211> LENGTH: 24
<212> TYPE: DNA
<213> ORGANISM: Artificial Sequence
<220> FEATURE:
<223> OTHER INFORMATION: Synthetic DNA

<400> SEQUENCE: 13
ccgcccgggt ccgaatgccc gcat                                                24

<210> SEQ ID NO 14
<211> LENGTH: 20
<212> TYPE: DNA
<213> ORGANISM: Artificial Sequence
<220> FEATURE:
<223> OTHER INFORMATION: Synthetic DNA

<400> SEQUENCE: 14
ccaggcaagg atggcgcacg                                                     20

<210> SEQ ID NO 15
<211> LENGTH: 28
<212> TYPE: DNA
<213> ORGANISM: Artificial Sequence
<220> FEATURE:
<223> OTHER INFORMATION: Synthetic DNA

<400> SEQUENCE: 15
cctgatcggc tccgccaatg tccatagg                                            28

<210> SEQ ID NO 16
<211> LENGTH: 20
<212> TYPE: DNA
<213> ORGANISM: Artificial Sequence
<220> FEATURE:
<223> OTHER INFORMATION: Synthetic DNA

<400> SEQUENCE: 16
gcagaggtgc tgcccagaac                                                     20

<210> SEQ ID NO 17
<211> LENGTH: 21
<212> TYPE: DNA
<213> ORGANISM: Artificial Sequence
<220> FEATURE:
```

<223> OTHER INFORMATION: Synthetic DNA

<400> SEQUENCE: 17
tcactccttg gatgccatgt g                           21

<210> SEQ ID NO 18
<211> LENGTH: 24
<212> TYPE: DNA
<213> ORGANISM: Artificial Sequence
<220> FEATURE:
<223> OTHER INFORMATION: Synthetic DNA

<400> SEQUENCE: 18
ggtaccttgg tggaaacttt gcgg                        24

<210> SEQ ID NO 19
<211> LENGTH: 24
<212> TYPE: DNA
<213> ORGANISM: Artificial Sequence
<220> FEATURE:
<223> OTHER INFORMATION: Synthetic DNA

<400> SEQUENCE: 19
ggtaccgtta caagaagcag actg                        24

<210> SEQ ID NO 20
<211> LENGTH: 24
<212> TYPE: DNA
<213> ORGANISM: Artificial Sequence
<220> FEATURE:
<223> OTHER INFORMATION: Synthetic DNA

<400> SEQUENCE: 20
agatactgct acgaaagacc ccga                        24

<210> SEQ ID NO 21
<211> LENGTH: 25
<212> TYPE: DNA
<213> ORGANISM: Artificial Sequence
<220> FEATURE:
<223> OTHER INFORMATION: Synthetic DNA

<400> SEQUENCE: 21
ctctcttggt tgtagccctc atctg                       25

<210> SEQ ID NO 22
<211> LENGTH: 25
<212> TYPE: DNA
<213> ORGANISM: Artificial Sequence
<220> FEATURE:
<223> OTHER INFORMATION: Synthetic DNA

<400> SEQUENCE: 22
gcggccgcag atactgctac gaaag                       25

<210> SEQ ID NO 23
<211> LENGTH: 24
<212> TYPE: DNA
<213> ORGANISM: Artificial Sequence
<220> FEATURE:
<223> OTHER INFORMATION: Synthetic DNA

<400> SEQUENCE: 23
gcggccgcct ctcttggttg tagg                        24

<210> SEQ ID NO 24

```
<211> LENGTH: 24
<212> TYPE: DNA
<213> ORGANISM: Artificial Sequence
<220> FEATURE:
<223> OTHER INFORMATION: Synthetic DNA

<400> SEQUENCE: 24
gcggccgcac agcccctgga ggag                                          24

<210> SEQ ID NO 25
<211> LENGTH: 25
<212> TYPE: DNA
<213> ORGANISM: Artificial Sequence
<220> FEATURE:
<223> OTHER INFORMATION: Synthetic DNA

<400> SEQUENCE: 25
gcggccgcgg tgatgtagat cagtc                                         25

<210> SEQ ID NO 26
<211> LENGTH: 24
<212> TYPE: DNA
<213> ORGANISM: Artificial Sequence
<220> FEATURE:
<223> OTHER INFORMATION: Synthetic DNA

<400> SEQUENCE: 26
gcggccgcga tactgctacg aaag                                          24

<210> SEQ ID NO 27
<211> LENGTH: 24
<212> TYPE: DNA
<213> ORGANISM: Artificial Sequence
<220> FEATURE:
<223> OTHER INFORMATION: Synthetic DNA

<400> SEQUENCE: 27
gcggccgcct ccaactctga taac                                          24

<210> SEQ ID NO 28
<211> LENGTH: 23
<212> TYPE: DNA
<213> ORGANISM: Artificial Sequence
<220> FEATURE:
<223> OTHER INFORMATION: Synthetic DNA

<400> SEQUENCE: 28
gcggccgcca gcccctggag gag                                           23

<210> SEQ ID NO 29
<211> LENGTH: 23
<212> TYPE: DNA
<213> ORGANISM: Artificial Sequence
<220> FEATURE:
<223> OTHER INFORMATION: Synthetic DNA

<400> SEQUENCE: 29
gcggccgctt aatcatcatc agc                                           23
```

FULL LENGTH POLYNUCLEOTIDE CODING CHICKEN TYPE II COLLAGEN AND THE USE OF IT

FIELD OF THE INVENTION

The present invention relates to a nucleic acid molecule as set forth in SEQ ID NO:1 comprising a polynucleotide sequence encoding full length chicken type II collagen (CCII), or a fragment thereof in possession of the same biological functions as well as CCII encoded thereof. It also relates to a method for producing CCII, and its use in the manufacture of a medicament for treating and/or preventing rheumatoid arthritis (RA). The invention specifically relates to a pharmaceutical composition for treating and/or preventing osteoarthritis and RA, to a food or beverage composition, and to a food additive composition, containing CCII prepared according to the method described in this invention, and the use of the nucleic acid molecules of the present application in gene therapy.

BACKGROUND OF THE INVENTION

RA, an autoimmune disease with a high incidence, can seriously threaten the health of the afflicted individual. Due to the limited knowledge concerning the etiology and pathogenesis of RA, controlling inflammation, alleviating the symptoms, and maintaining the functions of affected joints are the principal therapeutic aims when treating those diagnosed with RA. However, these treatments are far from the ultimate goal of preventing joint injury. With the development of novel molecular biology techniques in recent years, great progress has been made in our understanding of the pathogensis of RA, providing inroads into new therapeutic strategies.

In 1993, American scientists reported in for the first time their ability to successfully treat RA patients by using CCII (Trentham D E, Dynesius-Trentham R A, Orav E J, et al. Science, 1993, 261: 1727-1730), a finding which immediately attracted world-wide attention. Phase III clinical trials with CCII are underway in some developed countries, including America, Britain, and France. From a comprehensive analysis of the published literature we concluded that an oral tolerance approach, as a novel treatment, may increase our prospects for treating RA, by allowing investigation into both its root cause and symptoms (Trentham D E, Dynesius-Trentham R A, Orav E J, et al., Science, 1993, 261: 1727-1730).

To date, these clinical trials are only half-way toward completion and the pharmaceutical companies in developed countries are beginning to make CCII into an effective food additive to circumvent the laborious medication approval process. Though, internationally, natural CCII has been administered in studies of oral immunological tolerance for RA, its use in this manner also has severe drawbacks: 1) The quality of the obtained CCII differs from one company to another, as well as between batches from the same company, which makes it difficult to guarantee a consistent and continuous curative effect; 2) The continued extraction and preparation of CCII is time-consuming and requires a good deal of resources.

The inventor proposes a new approach, specifically a genetic engineering method for producing CCII, to solve the above-mentioned problems. We developed a technique to clone the CCOL2A1 gene, which can then be expressed efficiently in order to produce the recombinant CCII. The proposed invention relies heavily on the successful novel cloning of the polynucleotide sequence-CCOL2A1 cDNA encoding the full length CCII.

SUMMARY OF THE INVENTION

In one aspect, the present invention relates to an isolated nucleic acid molecule as set forth in SEQ ID NO:1, comprising a polynucleotide sequence encoding the full length CCII, or a fragment thereof in possession of the same biological functions.

In another aspect, the present invention also relates to CCII or the fragment thereof in possession of the same biological activity, which is encoded by the isolated nucleic acid molecule of the above-mentioned present application.

Additionally, the present invention relates to a recombinant expression vector containing the nucleic acid molecules encoding CCII, or a fragment thereof in possession of the same biological functions.

The present invention further includes the host cells transformed with the above-mentioned recombinant expression vectors, which is able to express CCII, or a fragment thereof in possession of the same biological activity.

The proposed invention further includes a method for producing CCII, comprising the following steps:
1) Transforming a suitable host cell by the recombinant expression vector with the present invention;
2). Culturing the host cells obtained in step 1) in suitable culture medium and under appropriate culture conditions;
3). Separating and purifying the proteins of interest from the culture medium or cell.

The present invention further relates to the use of CCII prepared according to the proposed invention in manufacture of a medication for treating and/or preventing RA.

The present invention is particularly relates to a pharmaceutical composition for treating and/or preventing osteoarthritis and RA, which contains a therapeutically effective amount of CCII prepared according to the methods in the present invention, and optionally, a pharmaceutically-accepted vehicle.

The present invention also includes a food or beverage composition, which contains a necessary amount of CCII prepared according to the method described in the present invention.

The present invention also relates to a food additive composition containing a certain amount of CCII prepared according to the above-mentioned method of present invention.

The present invention further describes the use of the said nucleic acid molecules and fragments thereof in gene therapy.

DETAILED DESCRIPTION OF THE INVENTION

Recently, oral tolerance, a specific immunotherapy, has become the most widely studied treatment regimen in treating autoimmune diseases. In general, the process includes oral administration of a protein antigen, which is subsequently used for parentetal immunization and which then arouses a mild immune response. It is believed that the development of oral tolerance is mediated by several factors, including self-cytoinhibition, clonal anergy and deletion, and bystander supression. Additional factors that determine the efficacy of the treatment include the dosage, origin, properties of the antigens, the present process of antigen, and the heredity and development of the individual receiving treatment.

We may therefore, conclude from a comprehensive analysis of the published literature that: 1) oral tolerance opens up a novel and promising way to treat RA by examining both its etiology and symptom profile; 2) oral tolerance of CCII produces a marked curative effect in many RA patients; 3) CCII is superior in its curative effects to other species-derived CII, because CCII is rich in chondroitin sulfate A and proteoglycans. The latter has the highest concentration of glucosamine sulfate, which possesses a powerful anti-inflammatory action and the ability to repair cartilage. In particular, 6- to 8-week-old chickens have the highest glucosamine sulfate; 4) CCII is also rich in proteoglycans with anti-oxidant activity (also known as cartilage matrix glycoprotein, CMGP), which reduces oxidation in chondrocytes; 5) CCII effectively prevents the proteasomal digestion of arthroidal cartilage, and restores the damaged chondrocytes and cytokines, thus remarkably lessening the incidence of inflammation; 6) CCII promotes the synthesis of both chondrocytes and proteoglycans, and also increases secretion of synovial fluid and hyaluronic acid in joints; 7) CCII is a potent anti-inflammatory agent and pain reliever; 8) CCII is safe and free of any toxicity or side effects, particularly when compared to any other RA drugs currently available.

At present, the immunological tolerance induced by oral administration of CCII has become an important novel treatment for RA. In order to provide sufficient amounts of high-quality CCII, we employed genetic engineering, instead of the traditional extraction and purification from the natural materials, to produce recombinant CCII.

The proposed invention involved the cloning of the CCOL2A1 gene, which was then expressed to produce recombinant CCII. In addition to the successful expression, this approach concurrently deepened our understanding of the CCOL2A1 gene. To date, human, canine and rat COL2A1 genes have been successfully cloned and localized on the chromosome, but studies that have cloned the full length CCOL2A1 cDNA and genome DNA, identified the location on the chromosome, described constitutive expression in various tissues, and induced expression of recombinant CCOL2A1 remain unavailable. These reports regarding the cloning of CCOL2A1 can provide great medicinal, therapeutic and economic value.

The cDNA sequence encoding CCII is relatively long, moreover, our understating about the functional region of the gene is greatly limited, thus it is very important to obtain the cDNA encoding the triple helical region of CCII. The application of PCR to isolate and amplify this gene is complicated in that CII has a complicated secondary structure, highly repetitive sequences, and a high GC content (mean GC content >70%, some as high as 80%) (Nah D H, Upholt W B., J Biol Chem, 1991, 266 34:23446-23452).

Therefore, the restriction site of the cDNA sequence in the CCII3' domain was analyzed, in which the cDNA was incompletely digested by the restriction enzyme, followed by a PCR amplification of the C-terminal domain of the digested cDNA. Because of the long cDNA sequence encoding CCII, we divided the cDNA into five fragments, and each fragment underwent a separate PCR amplification with overlap of at least 50 bp, to allow for a better end-to-end connection using SOE-PCR. Because of the high content of CC in genes encoding CCII, Taq enzyme, which is particularly suitable for the amplification of GC-rich content, was used.

The obtained full length CCOL2A1 cDNA was 4837 bp and consisted of an open reading frame (ORF) of 4260 bp and a 3' nontranslated region of 520 bp. The cDNA was inserted into a pGEM-T vector for sequencing, the results of which confirmed that the cDNA sequence was specific to CCOL2A1, which has thus far not been reported. The sequence has been admitted to GenBank database (AY046949).

The available literature indicates that the structure of the CCII genomic DNA is rather complicated, yet, to date no relevant studies on the CCOL2A1 genome DNA have explored this in detail. Therefore, following the successful cloning of the full length CCOL2A1 cDNA, we cloned and analyzed the CCOL2A1 genomic DNA. Because it contains a high content of OC, and frequently repeated sequences, as well as many nonspecific binding sites to the primers, we initially only obtained fragments (5494 bp) of the 3' end from the amplification of the chicken peripheral blood corpuscles-derived DNA through PCR (anti-coagulating with EDTA), but failed to obtain the gene of interest, regardless of the template, primer, or PCR amplification conditions utilized. Furthermore, we also failed to sequence the positive clones screened from the chicken DNA library due to the high GC content and PolyT structure.

In view of this, we next designed several primers for sequencing based on the known exon sequence, and succeed in sequencing the DNA of the CCOL2A1 genome. The obtained DNA sequence was 12003 bp long, contained 45 exons interrupted by 44 introns, which, as confirmed by a Genbank search, was unique to the CCOL2A1 genome, and had never been previously reported. The identified sequence has already been submitted to GenBank (Accession No: AF452711)

The sequence analysis of the CCOL2A1 genomic DNA clearly revealed that either the intron or the exon is remarkably smaller than in chicken type I and III collagen, consistent with the reports by Upholt (Ausar S F, Beltramo D M, Castagna L F, et al., Rhematol Int., 2001, 20:138-144); CII is highly conserved throughout evolution, its amino acid is 92% homologous in various species, and in some is 99% homologous. Based on this, we held that a short mean length of the introns, rather than a reduction in the overall number of introns, accounted for the compact CCOL21 gene.

To better understand the related genetic bioinformatics of CCOL2A1, and to gain insight into the evolutionary characteristics, homology was analyzed between the sequence of the full length cDNA of the cloned CCOL2A1 and the encoded proteins, and that of the triple helical region cDNA and proteins from dog (AF023169. AF242201), human (L10347), speckled dace (U23822), and rat (M65161), respectively, using MegAlign from Dnastar software. From this, the evolutionary trees were identified via Genedoc. The results revealed that CCII was most homologous to the canine CII (79.03% and 94.77% for the cDNA and amino acid, respectively), followed by the human CII (78.96% and 93.89%, respectively), and the rat CII (77.38% and 92.90%, respectively). However, among the five species that had been compared, human and canine CII share the greatest degree of homology (91.89% and 98.52% for the nucleotide and amino acid, respectively), with rat CII sharing the second greatest degree of homology (88.63% and 96.15%, respectively).

Following identification of the CCOL2A1 cDNA and genomic DNA, as well as the evolutionary characteristics of the gene, the next aim was an accurate localization of the CCOL2A1 gene on the chromosome. RH hybridization mapping, though recognized as the most precise method to localize a gene on its chromosome, was not possible with the CCOL2A1 gene as no chicken RH hybridization template is available from any suppliers. Thus chromosomes during the cell-division phase, derived from chicken peripheral blood corpuscles, were hybridized using our chromosome FISH technique, with digoxin-labeled gene fragments serving as the probes. As confirmed by the statistical analysis, genes encoding CCOL2A1 were located within the second region of the short arm of the chromosome 4 in chickens, and in chromosome 8 and 12 in rat and human, respectively. (Barnett M L, Combitchi D, Trentham D E. Arthritis & Rheumatism, 1996, 39 4:623-628)

It is widely known that collagens, with the exception of Type XI and II collagens, are broadly distributed throughout various organs, and usually share common chains. Type XI collagen contains polypeptide subunit α1, α2 and α3, the last being the product of α1(II) gene expression; therefore α3 differs from the α1 of type II collagen only in the content of hydroxyl lysine (Rousseau J C, Farjanel J, Boutillon M M, et al., J Biol Chem, 1996, 271(39): 23743-8). Type XIII collagen is a transmembrane protein of C II, so they are constituted of similar polypeptide residues (Snellman A, Keranen M R, Hagg P O, et al. J Biol Chem, 2000, 275(12):8936-44).

To understand the important role of CCOL2A1 in the evolution and development of the chicken embryo, RT-PCR and ELISA were employed to analyze comprehensively and systematically the expression of CCOL2A1 in both the embryos and mature tissues. Our results suggest that in embryos, CCOL2A1 mRNA is expressed in the heart, liver, vitreous body, cornea, skin, pectoral muscle, sternum, small intestine, arthroidal cartilage, meniscus, and skull, but not expressed in the spleen, thymus gland nor testicle. Detection of CCII protein levels in adult chickens reveals that, in addition to expression in the the sternum and arthroidal cartilage, CCII proteins are also expressed in both the spleen and small intestine; the highest level of expression is found in the arthroidal cartilage, followed by the sternum. However, it is important to note that in the process of detecting CCII expression, when digesting with pepsin and elastase, CII can generate an a chain short peptide. Because of this, collagen containing α1 (II) chains may bind with the monoclonal antibody of CCII, generating false-positive labeleing. As a result, the possibility that we simultaneously detected type XI and XII collagen was not excluded.

It should be emphasized that the splicing of the CCOL2A1 exons can be quite complicated, particularly the CII exon 2, as its splicing varies in different tissues. We therefore analyzed the splicing of exon 2 at the N-terminal domain from the cartilage tissues with high CII expression, including sternum and arthroidal cartilage, as well as non-cartilage tissues, such as heart, liver, pectoral muscle, small intestine, vitreous body, and cornea. In 17 day chickens, exon 2 was absent from the cDNA encoding CCII in sternum, meniscus, and arthroidal cartilage, but present in non-cartilage tissues, such as heart, liver, vitreous body, cornea, small intestine, muscle, skin and pectoral muscle. However, RT-PCR results indicated that exon 2 mRNA may be absent from the vitreous body and cornea. Furthermore, the vitreous body from the embryos <14 d contain only the second exon, which was notably absent at day 17 of embryological development. This is the first report of differential splicing of the exon 2 in various tissues.

The above-mentioned phenomena may be explained in that the second exon of CCII is absent in the cartilage tissues, but present in the non-cartilage tissues, such as the heart, liver, cornea, small intestine, muscle, and skin. In addition, regulatory sequences exist in CII collagen that can influence expressions of CII in different tissues and in different embryological stages as well. CCII, initially distributed extensively throughout the internal organs, is ultimately restricted only to cartilagenous tissues during chicken growth and development. Finally, abundant CCII is found in the sternum from the developing chicken embryos, which is gradually reduced due to the calcification of the cartilage (Young M F, Vogeli G, Nunez A M, et al., Nucleic Acids Res, 1984, 12 (10): 4207-4228; Marshall G E, Konstas A G P, Lee W R., Br J Ophthalmol, 1993, 77:515-524). Present views support the notion that CCII is expressed in both the vitreous body and in cartilage (Seery C M, Davision P F. Invest Ophthalmol Vis Sci, 1991, 32:1540-1550; Huerre-Jeanpierre C, Mattei M G, Weil D, et al., Am J Hum Genet, 1986, 38(1): 26-37), but this view conflicts with our findings that CCII is undetectable in the vitreous body.

To achieve the aim of the present invention, we succeeded in cloning the cDNA encoding CCII, and localized this gene to the chromosome. We also analyzed the gene expression prolife, cloning of the genomic DNA, and the bioinformatics of CCOL2A1. In particular, the successful cloning of the cDNA encoding full-length CCII is of great importance as it provides a solid foundation for the proposed invention, allowing us to produce recombinant CCII and subsequent novel therapeutic agents to treat RA, using genetic engineering approaches.

The present invention relates to the full length polynucleotide sequence comprising the nucleotides of SEQ ID NO: 1 encoding CCII, and/or the fragment in possession of the same biological functions.

The present invention also relates to CCII encoded by the isolated nucleic acid molecules, and/or the resulting fragment with the same biological functions, or a conserved variant thereof.

The "variant" of protein or polynucleotide refers to an amino acid sequence or polynucleotide sequence encoding the same having one or more amino acids or nucleotide modified. The modification here includes the deletion, insertion, or substitution of an amino acid or nucleotide. The variant may have conserved modifications in which the original sequence is replaced by another one of similar structure and chemical properties. Such an alteration may include, for example, substitution of leucine for isoleucine, or non-conserved changes, for example, a substitution of tryptophan for glycine.

"deletion" indicates one or more of the amino acids or nucleotides in the amino acid sequence or nucleotide sequence is deleted.

"Insertion" indicates the addition of one or more of the amino acids or nucleotides to the original amino acid or the nucleotide sequence.

"Substitution" indicates that one or more of the amino acids or nucleotides are replaced with various amino acid or nucleotide.

"Bioactivity" indicates that the proteins have the same structure, regulative or biochemical functions as the natural molecules;

"Similarity" indicates that the amino acid residue in the corresponding position should be the same, or conserved to a similar degree. The amino acid used in the conserved substitution includes: negatively-charged amino acids including aspartic acid and glutamic acid; positively-charged amino acids including lysine and arginine; amino acids with no electric charge and similar hydrophily to the head group, including leucine, isoleucine and valine; glycine and alanine; asparagine and glutamine; serine and threonine; phenylalanine and tyrosine;

"isolated" indicates the removal of the substance from its original environment, for example, a natural polynucleotide or polypeptide in the live animal is not separated. Similarly, a polynucleotide and polypeptide can be separated from some or all of its coexistent substances in the natural system. Such polynucleotide and polypeptide may be a part of the vector or the composition, which is also isolated because they are not a component of the natural environment.

The polynucleotide of the present invention may present as RNA or DNA, the latter includes cDNA, genomic DNA, and synthesized DNA. DNA can be double chains or the single chain (sense strand and/or antisense strand). The polynucleotide sequence encoding a polypeptide may be the same as in SEQ ID No.1, or a different sequence due to the redundant genetic code, which encodes the mature polypeptide in SEQ ID No.3.

The present invention further relates to a variant of the polynucleotide encoding the amino acid sequence, polypeptide fragment, and analogue of the SEQ ID NO.3. These include polynucleotide variants, natural allele variants, or unnatural polynucleotide variants.

The polynucleotide encoding the invented polypeptide was fused with a specific flag sequence in the same reading frame, which can promote purification of the polypeptide. When using a bacteria host, the flag sequence may be a histidine marker of the pQE vector, so as to promote the purification of the polypeptide fused with the marker, the flag sequence may also be a haemagglutinin (HA) marker from a mammalian host (such as COS-7 cell line of the monkey renal fibroblast). In addition, the polynucleotide sequences encoding the invented polypeptide may also consist of specific homologous or heterogenous sequences for the signal peptide, which can help with secretion of the proteins of interest out of the procaryotic cell or the eukaryotic cell membrane. The technicians involved in this project are aware that the above-mentioned flag sequence and the signal peptide sequence can be added to the vector expressing the polypeptide by recombinant methods or by a chemical process.

The present invention concerns the polynucleotide encoding the amino acid sequence of the SEQ ID NO: 3, the activate active fragment thereof, analog, and variant.

The present invention relates to the polypeptide amino acid of SEQ ID NO: 3 and the active fragment, analogue and deviant. The fragment with the same biological activity of SEQ ID NO: 3 polypeptide is a fragment with essentially conserved biological function.

The CCII prepared in this invention is a recombinant protein, polypeptide or fragment, derivative, and analogue. In particular, the polypeptide fragment, variant, or analogue of SEQ ID NO: 3, might be: (i) a polypeptide with one or several amino acid residues replaced by conservative or non-conservative amino acid residues (a conservative amino acid residue is preferable), where the replaced amino acid residue may or may not be encoded by the genetic code. For example, the mutant or the equivalent of CCII may be obtained by inserting, replacing and/or deleting the amino acid residue. The conservative replacement is based on the similarity in terms of the equivalent charge, solubility, hydrophobicity, and/or amphipathy of the amino acid residues, as long as it maitains the activity of CCII; or (ii) a polypeptide with one or several amino acid residues containing a substituted group; or (iii) a mature polypeptide or other functional compound, such as the polypeptide fused by compounds (for example polyethylene glycol) capable of increasing the half life of the polypeptide; or (iv) a mature polypeptide and polypeptide fusing with other amino acid sequences which render the amino acid and protein sequence helpful in purifying the mature protein. The structures helpful to purification include NTA mealty affinity chromatography, such as the histidine-tryptophan module for purification on the immobilized metal; protein A structure field for purification of the immobilized immunoglobulin, and structure fields for the FLAGS extension/affiliation purification system (IMMUNEX company, Seattle, Wash.). The junction sequence specific to XA enterokinase is also helpful in the protein purification (Porath, J. et al. (1992), Prot. Exp. Purif. 3:263-281).

The CCII in the text of the present invention comprises the CCII of SEQ ID NO: 3, i.e., mature polypeptide, the polypeptide having at least 90% similarity to the polypeptide of SEQ ID NO: 3, 90% identity is preferable), and more preferable, having ate least 95% similarity, and 95% identity is preferable. It also includes part of said polypeptide containing at least 30 amino acids, preferably having more than at least 50 amino acids.

The polypeptide, the conservative variant thereof, and the bioactive fragment and variant thereof, can be prepared by routine synthesis of peptides, such as solid phase synthesis of peptides (Merrifield J. (1963), J. Am. Chem. Soc. 85:2149-2154; Roberge, J. Y. et al. (1995) Science, 269:202-204). The synthesis of the proteins can be performed by hand or by using Applied Biosystems 431A Perkin Elmer. CCII in this invention may also be obtained from the separation and purification of the natural biomaterial, but DNA recomposition using the polynucleotide is preferable.

Based on routine DNA recombination, the polynucleotide sequence of present invention was used to express or prepare the recombinant CCII, thus the present invention relates to the method for producing CCII of the present invention. The method included:

(1) Transforming the host cell by the polynucleotide (or its variant) encoding CCII, or the recombinant vector containing the polynucleotide.
(2) Culturing the host cells under proper conditions and in proper culture medium
(3) Separating and purifying the proteins of interest from the culture medium or cells The present invention also relates to the recombinant vector containing polynucleotide, host cells containing the vector, and the preparation of the polypeptide by recombinant techniques.

The polynucleotide can be used to produce polypeptides using various recombinant techniques. For example, the polynucleotide may exist on any vector selected to express the polypeptide, including chromosomal, non-chromosomal and synthesized DNA sequences, such as the SV40 variant, bacterial plasmid, phage DNA, zymoid plasmid, vectors derived from binding of the plasmid and phage DNA, virus DNA, baculovirus, cowpox virus, adenovirus, fowlpox virus and PRV, and also including, but not restricted to, pQE series (Qiagen), pBS, pD10, phagescript, psiX174, pBluescript SK, pBSKS, pNH series (Stratagene), pTRC99a, pKK223-3, pDR540, pRIT5 (Pharmacia); pWLNEO, pSV2CAT, pOG44, pXT1, pSG (Stratagene), pSVK3, pBPV, pMSG, pSVL (Pharmacia). However, any plasmid or vector can be used only if they can reproduce and survive in the host.

The present invention also includes the resulting recombinant construct containing the invented polynucleotide, including vectors, such as the above-mentioned plasmid or virus vector, into which the polynucleotide sequence is inserted in the forward or reverse orientation. The construct also contains the regulatory sequence, for example the promoter effectively connected to the polynucleotide sequence (including the constitutive and induced promoter), and mediates the transcription of the down-stream sequence. The promoters include, but are not restricted to: the PL promoter of λ phage, the protein promoter of the baculovirus polyhedron; bacteria promoters, such as LacI, LacZ, T3, T7, gpt, λPR, PL and trp; eukaryotic promoters, such as CMV early promoter, HSV thymidine kinase promoter, early and late SV40 promoter, retronituse virus LTR and rat metallothioneinI promoter; and also promoters derived from the plant genome such as heat shock protein (HSP) and RUBISCO promoter.

The expression vector contains binding sites for ribosomes and the transcription terminator needed for initiating translation, and also the proper sequence to promote the expression, such as an enhancer, a cis-acting factors for DNA, of about 10-300 bp, which stimulates the promoter, for example, an enhancer of 100-270 bp after the replication origin in SV40, the enhancer of the early cytomegalovirus promoter, the polyoma enhancer at the posterior side of the replication origin, and the adenovirus enhancer. In addition, the preferable vector also includes one or several selective resistance and/or marker genes that provide phenotypic features to facilitate screening of the transformed host cells; selective genes, such as trpB and hisD are helpful when using indole or histidinol (Hartman, S. C., and R. C. Mulligan (1988) Proceedings of the National Academy of Sciences, USA 85:8047-51), herpes virus TK and APRT for tk- or aprt-cells (Wigler, M. et al. (1977) Cell 11:223-32) (Lowy, I. et al. (1980) Cell 22:817-23); resistance genes, such as dihydrofloic acid reductase DHFR endow the methotrexate with resistance (Wigler, M. et al (1989), Proceedings of the National Academy of Sciences, USA, 77:3567-70) or npt which endows the neomycin and G-418 with resistance (Colbere-Garapin, F. et al. (1981) J. Mol. Biol., 150:1-14), as well as the tetracycline and ampicillin resistance genes. Mammalian expression vectors generally consist of replication origin, promoter, enhancer, and necessary binding sites for ribosomes, polyadenylation sites, the sites for assembling the donor and receptors, transcription termination sequences, and 5' flanked nontranscription sequences. DNA of the SV40-derived assembling sequence and polyadenylation site might provide the necessary nontranscription genetic elements. In addition, vectors containing the polypeptide sequence encoding the polypeptide might also contain specific homologous or heterogenous sequences of the signal peptide, which can aid secretion of the proteins of interest from the procaryotic cells or the eukaryotic cytolemma. Our technicians are aware that the flag sequence and signal peptide in the vectors and construct can be added to the polynucleotide by various recombinant or chemical methods.

A skilled person in the art should be familiar with how to choose a proper vector and promoter. Vectors for bacteria can be constructed as follows: the DNA sequences encoding the proteins of interest, along with the translation initiating and terminating signals, are inserted into an operable reading frame containing a promoter. It is also well known to a skilled artisan how to construct the nucleotide sequence, as well as the transcription and translation regulatory elements. These methods include in vitro DNA recombination, synthesis, and in vivo genetic recombination (Sambrook, J. (1989), Molecular cloning: a laboratory manual, Cold Spring Harbor Press; Plainview, N.Y.; Ausubel, F. M. (1989) Current Protocols in Molecular Biology, John Wiley & Sons, N.Y.).

Vectors containing the above-mentioned DNA sequence, promoter, or controlling sequence are suitable to transform the host to express the protein.

It is also within knowledge for a skilled person in the art how to choose a proper host to express the proteins of interest based on the category and the characteristics of the vector. The hosts suitable for expressing polypeptide include, but are not restricted to: a pronucleus host, such as colibacillus, bacillus, streptomyces; a eukaryotic host, such as saccharomyces, aspergillus; insectan cells, such as fruit fly S2 and noctuid Sf9; animal cells such as CHO and COS (Gluzman) (Cell 23:175, 1981) and other cell lines that can express the vectors, such as C127, 3T3, CHO, HeLa, BHK, Bowes melanoma cells; Botanic cells, adenovirus, etc. In addition, various culture systems of mammalian cells are also suitable for expressing recombinant proteins.

The recombinant products were obtained by inserting the vector or the construct containing the above-mentioned nucleotide sequence into the host cells, using the traditional methods, such as calcium chloride mediated transformation, calcium phosphate transfection, DEAE-dextran mediated transfection, electroporation, microinjection, bombard of particles, or using a particle gun, which should be performed by a trained individual. (Sambrook, J. (1989), Molecular cloning: a laboratory manual, Cold Spring Harbor Press; Plainview, N.Y.; Ausubel, F. M. (1989) Current Protocols in Molecular Biology, John Wiley & Sons, N.Y.; Hobbs, S. et al., McGraw Hill Yearbook of Science and Technology (1992) McGraw Hill, N.Y. 191-196; Engelhard, E. K. et al, Proceedings of the National Academy of Sciences, USA, 91:3224-3227; Logan, J. et al, Proceedings of the National Academy of Sciences, USA, 81:3655-3659).

The transformed host strains or cells are cultured to the appropriate cell density, and then the selected promoters are induced using the proper methods, such as altering temperature, and the addition of chemicals. The cells are then further cultured by trained individuals.

Under the control of the proper promoter, the mature proteins can be expressed in mammalian cells, yeast, bacteria, and various other cell types as well. They can also be produced from the DNA construct-derived RNA by using a cell-free translation system. (Sambrook, J. (1989), Molecular cloning: a laboratory manual, the $4^{th}$ part, $18^{th}$ chapter, Cold Spring Harbor Press; Plainview, N.Y.)

The cells and the culture solutions are generally harvested by means of centrifugation. When the proteins of interest are contained within the cells, any convenient physical, chemical, or enzymatic methods can be used, including recurrent freezing-melting, ultrasonication, mechanical crush, using cell solvent or specific smudge cells. In this case, the crude extraction is preserved for future purification. When the proteins of interest are secreted out of the cells, routine methods can be used to harvest them directly from the supernatant. The above-mentioned methods should be within the knowledge of a skilled artisan.

The methods to recover and purify the polypeptide from the recombinant cell cultures include ammonium sulfate and ethanol deposition, acid extraction, ion-exchanging chromatography, volume exclusion chromatography, hydrophobic interaction chromatography (HIC), affinity chromatography, hydroxyapatite chromatography, and phytoagglutinin chromatography. Overlap between the proteins is needed in order to allow for them to form their native conformation. Usually, high performance liquid chromatography (HPLC) and capillary electrophoresis (CE) can be used in the final purification step.

The present invention relates to the pharmaceutical use of the CCII prepared from a polynucleotide sequence in treating and/or preventing RA, including the encoding regions or partial fragment of the nucleic acid molecules, such as full length sequences, partial sequences, and mutant, all of which could effectively express CCII or the functional fragment thereof.

The present invention relates to a pharmaceutical composition for treating and/or preventing osteoarthritis and RA, containing a therapeutically effective amount of CCII prepared according to the methods described in this invention, and optionally, a pharmaceutically accepted vehicle.

The present invention also relates to a food or beverage composition, which is characterized by containing certain amount of CCII prepared according to the method described in this invention. The health food or additive made from CCII will be determined to be beneficial to osteoarthritis and RA.

The present invention relates to a food additive composition containing certain amount of CCII prepared following the methods described in this invention.

The present invention also relates to the usage of the nucleic acid molecules or the fragment thereof in gene therapy.

BRIEF DESCRIPTION OF THE DRAWINGS

FIG. 1 illustrates the PCR cloning of the genes encoding CCII in the present invention.

FIG. 2 illustrates the structure of the full length CCII in the present invention.

FIG. 3 contains PCR results of the 3' untranslated region (UTR) of genes encoding CCII from chicken embryos FIG. 4 illustrates the tissue specificity of the genes encoding CCII.

FIG. 5 is a graph showing the standard curve of CCII concentration-absorbancy.

FIG. 6 is an analysis of the splicing of the exon of the genes encoding CCII

FIG. 7 illustrates the chromosome band of the genes encoding CCII.

FIG. 8 is the division phase of the chromosome

FIG. 9 shows the results of ISH hybridization,

FIG. 10 is a homologous comparison of the evolutionary tree between human being, dog, rat, chicken and speckled dace.

FIG. 11 is the western blot analysis of the expression products in the supernatant and cytoplasm induced by pPIC9K/CCOL2A1 (A) and pPICZαB/CCOL2A1 (B). M is the protein marker, 1-5 is positive band and 6 is blank vector control.

FIG. 12 is the WB analysis of the co-expression of pPIC-ZαB/CCOL2A1/GS115 and pPIC9K/P4Hα pPIC9/P4Hβ. M is the protein marker, 1-5 is positive band and 6 is blank vector control.

The following examples are set forth by way of illustration and not intended to limit the scope of the present invention.

The protocols for the included techniques, including molecular biology, biochemistry and immunology, were all followed from a guide to Molecular Cloning, 2nd edition; digestion conditions for restriction enzymes and buffer were used according to the manufacturers' specifications. The incubation time was 1 h at 37° C. unless otherwise stated and in those cases were changed according to manufacturers' instructions.

EXAMPLE 1

Total RNA Extraction from Chicken Embryo Sternum

After the eggs had been sterilized, 17-day old SPF chicken embryos (Institute of Animal Sciences, Chinese Academy of Agricultural Sciences) were harvested and washed in cold saline. The sterum was isolated and grinded in TRIzol reagents on ice, followed by incubation in 1.5 ml eppendorf tube at room temperature for 10 min, centrifugation at 1000×g for 10 min at 4° C. The supernatant was transferred to a DEPC-treated eppendorf tube. To each tube was added 200 µl chloroform, followed by extraction mixture, incubation at room temperature for 10 min, and centrifugation at 1000×g for 10 min at 4° C. The aqueous phase was transferred to a new eppendorf tube. To each tube was added the same volume of isopropanol, followed by incubation at room temperature for 10 min, centrifugation, washing with 75% ethanol, Rnase-free water dissolving and storage at −80° C. for reverse transcription.

cDNA Synthesis cDNA was synthesized from total RNA using a oligodT-3 sites adaptor primer in a 3'RACE kit (TAKARA) as the antisense primier. Following revese transcription, the mixture was incubated at 95° C. for 5 min to inactivate the reverse transcriptase. The cDNA was kept at −20° C. for further experiments.

PCR Amplification of cDNA Encoding CCOL2A1 C-Terminal Propeptide

According to known CCOL2A1 C-terminal UTR sequences (Sandell L J, Prentice H L, Kravis D, Upholt W B., J Biol Chem, 1984, 259 (12) 7826-7834), sequence encoding of the CCOL2A1 C-terminal propeptide was amplified using col2a1-2F and col2a1-2R primers (Table 1). PCR reactions were carried out in 50 µl final solutions including 1 µl (20 pmol/µl) of each primer, 10×PCR buffer, 5 µl of 25 mM $MgCl_2$, 1 µl of 10 mM dNTPs, 2.5 µl of 100% glycerine (final concentration 5%), 2 µl cDNA, and 0.8 µl Taq polymerase. The PCR conditions were 96° C. for 10 min, then 30 cycles of 96° C. for 1 min, 62° C. for 1 min, 72° C. for 3 min and a final extension at 72° C. for 7 min. The amplified products were separated on a 1% agarose gel, recovered using a gel extraction kit (Invitrogen), cloned into a pGEM-T Easy vector (Promega), transformed into DH5α and sequenced by the ABI 377 autosequencer.

CCOL2A1 3'UTR cDNA Cloning

According to the known CCOL2A1 gene sequence, a CCOL2A1 3'UTR sense primer col2a1-1F (Table 1) was designed and amplified. Using the 3'RACE strategy, the corresponding 3 sites adaptor primer (col2a1-1R) was reverse-transcribed to amplify the 3'UTR. The reaction mixture included the PCR buffer and primer col2a1-1R with 3 site adaptor primers. The PCR conditions were 4 cycles of 96° C. for 1 min, 62° C. for 1 min, 72° C. for 30 s, then 26 cycles of 96° C. for 30 s, 62° C. for 30 s, 72° C. for 20 s and a final extension at 72° C. for 7 min. Amplified products were recovered and transformed as described above.

CCOL2A1 N-Propeptide cDNA Cloning

The gene encoding the 5'N propeptide was amplified using the sense primer col2a1-5F and antisense primer col2a1-5R. The PCR was performed in PCR buffer, and the annealing and extension steps were conducted at the same temperature. The PCR condition was 30 cycles of 96° C. for 5 min, 96° C. for 1 min, 72° C. for 50 s and a final extension at 72° C. for 7 min.

Construction and Sequencing of Recombinant Plasmid Vector

Plasmid extraction, restriction enzyme digestion, gel extraction, ligation, transformation, construction of recombinant plasmid and identification were performed according to Molecular Cloning, 2nd edition (Sambook J, Fritsch E F, Maniatis T. Molecular cloning: a laboratory manual. 2nd edition Cold Spring Harbor Laboratory Press, 1989). The constructed CCOL2A1 cDNA fragments, SOE ligated CCOL2A1 cDNA fragments and full-length CCOL2A1 were inserted into pGEM-T (Promega). The inserts were identified by restriction enzyme digestion followed by sequencing.

Plasmid Construction and Preparation

PCR products were recovered using a quick gel extraction kit and were separated by electrophoresis in a 1% agarose gel.

Amplified bands were cut out of the gel, and target genes were recovered using a quick gel extraction kit. The process is as follows:
1) The gel containing target gene was put in an eppendorf tube, added 1 ml of L1 solution and incubated in water bath at 50° C. for 15 min, completely dissolving the gel.
2) The dissolved gel was added to a column for centrifugation at 10000×g for 2 min followed by the addition of 500 μl of L1, incubation at room temperature for 1 min and centrifugation as described above.
3) 700 μl of L2 was added to the mixture, incubated at room temperature for 5 min and centrifuged as described above.
4) The mixture was further centrifuged at 10000×g for 2 min resulting in volatilizing ethanol.
5) The column was transferred to a new eppendorf tube, followed by the addition of 30 μl of hot (~70° C.) TE buffer, incubation at room temperature for 2 min, and centrifugation at 10000×g for 2 min. The purified target DNA was passed through into the collection vial. DNA recovered from the gel was separated by electrophoresis on a 1% agarose gel, and the confirmed concentration was 40 μg/μl.

Ligation of target DNA and pGEMT vector: 10 (1 of ligation system containing 5 (1 of 2× ligation buffer, 3 (1 of target DNA, 1 (1 T vector, 1 (1 of T4 DNA ligase was mixed and incubated at 4° C. ° C. overnight.

The competent. *E. coli*. DH5A was prepared as described by Molecular Cloning, 2nd edition.

The recombinant construct was used to transform DH5α competent cells: 4 (1 of the above constructed vectors pGEMT-col2a1-1 ((2, 3, 4, 5 etc.)) were added into 100 (1 of freshly prepared competent cells, incubated on ice for 30 min, hotheat-shocked at 42° C. for 90 s, followed by incubation in ice-water for 2-3 min, addition of 900 μl of LB without ampicillin, shaking at 160 rpm for 45 min at 37° C., and addition of 4 μl of 1 M IPTG and 16 (1 of 50 mg/ml X-gal on an LB/Ampicillin agar plate. The *E. coli* with that contained the inserts was were spread on the plate, incubated at 37° C. for 16 h until a suitable size of colonies appearing.

Screening of Positive Transformants

White colonies on ampicillin LB plate with IPTG/X-gal were picked up, and inoculated in LB solution with 200 μg/ml ampicillin, incubated with shaking at 37° C. (200 rpm) for 12 h, followed by plasmid extraction.

Step 6: Screen a Selected Few White Colonies.

Using above described method, the present invention produced pGEMT-col2a1-2, pGEMT-col2a1-1, pGEMT-col2a1-3, pGEMT-col2a1-(1+2), pGEMT-col2a1-5 and pGEMT-col2a1-4.

The positive colonies were identified by cutting the plasmid in 20 μl of digestion system containing 1 (1 of 10×Not I and Nco I restriction enzymes, 1 (1 of 0.1% BSA, 8 (1 of plasmid and 8 (1 of water using a Promega A7500 kit. The mixture was incubated at 37° C. for 2 h, followed by electrophoresis on a 1% agrose gel and sequencing by the ABI 377 autosequencer.

Splice overlap extension-polymerase chain reaction (SOE-PCR) of full-length chicken CCOL2A1 cDNA In order to obtain of full-length CCOL2A1 cDNA, this research the described research used use a SOE-PCR strategy for the construction ((Horton R M, Hunt H D, Ho S N, et al. Gene, 1989, 77:61-68)). This procedure needed four-time required four phases of PCR. The first PCR reaction used pGEMT-col2a1-2, pGEMT-col2a1-1 PCR products as templates, col2a-2F and col2a1-1R as sense and antisense primers and Pfu DNA polymerase to link products together resulting in products col2a1-(2+1). The PCR conditions were 4 cycles of 96° C. for 5 min, 96° C. for 1 min, 60° C. for 1 min and 72° C. for 150 s, then 26 cycles of 96° C. for 30 s, 58° C. for 30 s, 72° C. for 130 s and a final extension at 72° C. for 7 min.

The second PCR used plasmids pGEMT-col2a1-3, pGEMT-col2a1-(1+2) PCR as templates, col2a-3F and col2a1-1R as sense and antisense primers. The PCR conditions were 4 cycles of 96° C. for 5 min, 96° C. for 1 min, 64° C. for 1 min, 72° C. for 120 s then 26 cycles of 96° C. for 30 s, 62° C. for 1 min, 72° C. for 90 s and a final extension at 72° C. for 7 min.

The third PCR used col2a-5F and col2a1-4R as sense and antisense primers, col2a1-5 and col2a1-4 plasmid PCR products as templates. The PCR conditions were 4 cycles of 96° C. for 5 min, 96° C. for 1 min, 62° C. for 2 min, 72° C. for 120 s, then 26 cycles at 96° C. for 1 min, 60° C. for 1 min, 72° C. for 90 s and a final extension at 72° C. for 7 min.

The 4th PCR used col2a-5F and col2a1-1R as sense and antisense primers, former 3-time PCR-linked PCR products (col2a1-5+4, col2a1 1+2+3) as templates, resulting in full-length col2a1 cDNA. PCR conditions were 4 cycles of 96° C. for 5 min, 96° C. for 1 min, 62° C. for 2 min, 72° C. for 210 s, then 26 cycles at 96° C. for 1 min, 62° C. for 1 min, 72° C. for 280 s and a final extension at 72° C. for 7 min The primers used for cloning full-length chichen CCOL2A1 cDNA are shown in Table 1

TABLE 1

Primer sequences for amplifying full-length chichen CCOL2A1 cDNA

| | |
|---|---|
| col2a1-1F | 5'-TCT ATC GCG CAC CCG TTG TGC-3'; SEQ ID No. 4 |
| col2a1-1R | 5'-GTC TTG TAG TGC TAC GGC TTG C-3'; SEQ ID No. 5 |
| col2a1-2F | 5'-TTG CAG ATG TCT CCA ATA CCA G-3'; SEQ ID No. 6 |
| col2a1-2R | 5'-GCA CAA CGG CTC GGG CAA TGT GCT AAC G-3'; SEQ ID No. 7 |
| col2a1-3F | 5'-GCT CGG AAG CAA CGG CCT CG-3'; SEQ ID No. 8 |
| col2a1-3R | 5'-CTC GTC CCG GAC GCG ACG G-3'; SEQ ID No. 9 |
| col2a1-4F | 5'-CGC TGC GAT CGT CAT GCG G-3'; SEQ ID No. 10 |
| ool2a1-4R | 5'-GTA GTG ACC CTA CGC CCG AG-3'; SEQ ID No. 11 |
| col2a1-5F | 5'-ACG CCG GCT CTC GTG CTC CTC GTG GTG C-3'; SEQ ID No. 12 |
| col2a1-5R | 5'-CCG CCC GGG TCC GAA TGC CCG CAT-3'; SEQ ID No. 13 |

The present invention, utilized a SOE-PCR strategy to obtain full-length chicken CCOL2A1 cDNA. Due to the high GC content in the chicken CCOL2A1 gene, the buffer suitable for amplifying high GC content was used in the reaction system during the amplification procedure. The amplified products possessed high specificity and were inserted into pGEM-T vectors. The vectors were replicated in *E. coli* DH5, digested by the restriction enzymes provided by Promega, transformed and sequenced. The primers described above were synthesized by Shanghai Bioasia Biotech Co, and sequencing was performed by Takara Co. (Dalian, China). The results are shown in the sequencing list in SEQ ID NO:1.

EXAMPLE 2

Preparation Chicken Genomic DNA

Chicken genomic DNA was extracted using a Wizard genomic DNA purification kit (Promega) according to the manufacturer's instructions. The purity of the extracted DNA was 1.6-1.8 of 260/280 OD value using a spectrophotometer (BECKMAN, DU®640).

PCR-Based Cloning and Library Screening of Chicken CCOL2A1 Genomic DNA

PgF and PgR were used as sense and antisense primers for CCOL2A1 C-terminal cloning. The sequences of primers were as follows: PgF 5' CCA GGC AAG GAT GGC GCA CG 3' (SEQ ID No.14) ; PgR 5'CCT GAT CGG CTC CGC CAA TGT CCA TAG G 3'

(SEO ID No.15). PCR of CCOL2A1 genomic DNA was performed using LA Taq polymerase in GC buffer. PCR products were examined by 0.8% agarose gel electrophoresis, target gene fragments were recovered from gel slices using a gel extraction kit, and inserted in pGEM-T vectors. The inserts were identified by restriction enzyme digestion and sequencing. Due to the high GC content in the CCOL2A1 genomic DNA and polyT structure, fragment cloning of N-terminal of CCOL2A1 genomic sequences were performed by the SOE-PCR method using the total DNA extracted from whole blood and spliced to generate a nearly full-length CCOL2A1 genomic DNA sequence.

Initially, we amplified the DNA extracted from peripheral chicken blood via PCR to obtain a 5494 bp fragment at the CCOL2A1 3' end, and the specificity of the amplified products was very high (FIG. 1-9). The fragment was inserted into a pGEM-T vector to get pGEM-T/CCOL2A1 and confirmed by sequencing.

The results of sequencing revealed that the 3' ends of the chicken CCOL2A 1 genomic DNA contained a partial triple helix-forming region, 3'-terminal peptide and propepide. The cloned genomic regions contained 19 introns and 20 exons.

However, of the genomic sequences beyond the 3' end, regardless of templates, primers and PCR conditions used, the target gene sequences could not be obtained. Afterwards, the positive colonies screened from the genomic chicken DNA library were sequenced, but high GC content and PolyT structure restricted the process of sequencing, resulting in a sequencing signal interrupt.

Therefore, we utilized known exon sequences to design numerous primers to complete the CCOL2A1 genomic DNA sequencing. Finally, we obtained a 12523 bp length CCOL2A1 genomic DNA sequence containing 54 exons and 53 introns. The exons and introns are shown in Table 2. The structure of the obtained chicken COL2A1 3' end gene is shown in FIG. 2. After accessing the database, it was clear that the genomic DNA sequences specifically belonged to the CCOL2A1 genome, and had not yet been reported. The relevant gene sequences have been submitted to GenBank (Accession No. AF52711).

TABLE 2

The structure of exons and introns of the 3' genomic chicken COL2A1 DNA

| Exon | Amino acid coding region | Exon sizes (bp) | Intron sizes (bp) |
|---|---|---|---|
| 1 | 1-30 | >135 | ND |
| 2 | 31-100 | 210 | ND |
| 3 | 101-117 | 50 | ND |
| 4 | 118-146 | 87 | ND |
| 5 | 147-180 | 102 | ND |
| 6 | 181-206 | 78 | ND |
| 7 | 207-221 | 45 | ND |
| 8 | 222-239 | 54 | ND |
| 9 | 240-258 | 54 | 124 |
| 10 | 259-274 | 54 | 107 |
| 11 | 275-292 | 54 | 100 |
| 12 | 293-310 | 54 | 98 |
| 13 | 311-325 | 45 | 86 |
| 14 | 326-343 | 54 | 110 |
| 15 | 344-358 | 45 | 86 |
| 16 | 359-376 | 54 | 113 |
| 17 | 377-409 | 99 | 89 |
| 18 | 410-424 | 45 | 198 |
| 19 | 425-457 | 99 | 367 |
| 20 | 458-475 | 54 | 885 |
| 21 | 476-511 | 108 | 408 |
| 22 | 512-529 | 54 | 88 |
| 23 | 530-562 | 99 | 91 |
| 24 | 563-580 | 54 | 682 |
| 25 | 581-613 | 99 | 82 |
| 26 | 614-631 | 54 | 82 |
| 27 | 632-649 | 54 | 124 |
| 28 | 650-667 | 54 | 277 |
| 29 | 668-685 | 54 | 79 |
| 30 | 686-700 | 45 | 114 |
| 31 | 701-733 | 99 | 262 |
| 32 | 734-769 | 108 | 92 |
| 33 | 770-787 | 54 | 80 |
| 34 | 789-805 | 54 | 81 |
| 35 | 806-823 | 54 | 82 |
| 36 | 824-841 | 54 | 94 |
| 37 | 842-877 | 108 | 89 |
| 38 | 878-895 | 54 | 108 |
| 39 | 896-913 | 54 | 113 |
| 40 | 914-967 | 162 | 268 |
| 41 | 968-1003 | 108 | 92 |
| 42 | 1004-1039 | 108 | 309 |
| 43 | 1040-1057 | 54 | 160 |
| 44 | 1058-1093 | 108 | 97 |
| 45 | 1094-1111 | 54 | 268 |
| 46 | 1112-1147 | 108 | 109 |
| 47 | 1148-1165 | 54 | 134 |
| 48 | 1156-1201 | 108 | 79 |
| 49 | 1202-1297 | 289 | 78 |
| 50 | 1298-1360 | 188 | 407 |
| 51 | 1361-1441 | 243 | 594 |
| 52 | 1442-1489 + 520 bp 3'UTR | 667 | 112 |

Notes:
Exon and introns were named according to the method described by Upholt et al. (J Biol Chem, 1984, 259(12); 826-7834).

CCOL2A1 Expression Spectrum in the Chicken Embryo

CCOL2A1 3' UTR was confirmed to specially belong to CCOL2A1 via Blast database searching. Therefore, the CCOL2A1 cDNA 3'UTR was used as an amplifying subject to investigate aI (II) expression in the developing chicken embryo. Heart, liver, vitreum, cornea, skin, pectoralis, sternum and etc. in 17-day old chicken embryo were analyzed using RT-PCR. The primers were col2a1-1F and col2a1-1R, listed in Table 1. The PCR products were inserted into a pGEMT-easy vector and sequenced after restriction enzyme digestion. Simultaneously, GAPDH was amplified as an internal control using the primers $PF_{GAPDH}$ 5' GC AGA GGT GCT GCC CAG AAC 3'(SEQ ID No.16); $P_{RGAPDH}$ 5' TCA CTC CTT GGA TGC CAT GTG 3' (SEQ ID No.17) to generate a 412bp GAPDH fragment.

Using the results obtained from the RT-PCR of 17-day-old chicken embryo CCOL2A1 3' UTR, chicken embryo CCOL2A1 mRNA was expressed in heart, liver, vitreum, cornea, skin, pectoralis, sternum, small intestine, arthrodial cartilage, meniscus and cranial bone, but was not detected in spleen, thymus and testis (FIG. 3).

Expression Spectrum of Adult Chicken Type II Collagen

Type II collagen in heart, liver, spleen, kidney, vitreum, cornea, skin, pectoralis, meniscus, pancreas, thymus, small intestine, stomach, testis, skeletal muscle, cerebrum, cerebellum, arthrodial cartilage, sternum and lung of 4-week-old chicken was analyzed by ELISA using a natural type II collagen test kit (Chondrex). Five mg of each frozen sample was homogenized and dissolved in 0.8 ml of 50 mM acetic acid-0.2 M NaCl (pH 2.9-3.0), digested in 100 µl of 20 mg/ml pepsase (Sigma) at 4° C. for 48 h followed by addition of 250 µl of 10×TSB, The pH was adjusted to 8.0 using M NaOH, samples were incubated in 100 (1 of 2 mg/ml elastase (Sigma) at 4° C. ° C. overnight, centrifugation and centrifuged at 10000×g for 5 min at 4° C. ° C. The precipitate was discarded, the volume of the supernatant was adjusted to 1 ml and, discharging precipitation, adjusting the supernatant to 1 ml and stocked at 4° C. for future experiments.

The extracted chicken type II collagen was analyzed by sandwich ELISA. Two monoclonal antibodies against different epitopes of the chicken type II collagen molecule were used. One was used as a coating antibody, and the other was used as the enzyme-labeled detecting antibody. First, an ELISA plate was coated with the capture antibody at 4° C. overnight, followed by 3 washes, 1:200 dilutions of the samples, loading samples and standards onto the coated ELISA plate, incubation at 37° C. for 2 h, washing as described above, adding biotin-labeled anti-chicken type II collagen monoclonal antibody to each well, incubation at 37° C. for 2 h, washing as described above, adding enzyme-conjugated streptavidin, incubation at 37° C. for 1 h, washing vigorously, adding OPD solution at 37° C. for color development, stopping the enzyme reaction by 1.25 M sulfuric acid and analyzing the OD490 value. The detailed protocol was described in the kit's instructions (The Arthrogen-CIA® native type II collagen detection kit (Chondrex)).

The results of the natural type II collagen analysis in 20 organs of adult chickens showed that chicken type II collagen is expressed in sternum, arthrodial cartilage, pancreas and small intestine, but not in other organs (FIG. 4).

Using chicken natural type II collagen as a standard, a concentration vs absorbance standard curve was made to calculate the expression level of chicken type II collagen in relevant positive tissues (FIG. 5).

Based on the standard curve, the expression level of chicken type II collagen was 0.4% in sternum, 1.5% (the highest level in arthorodial cartilage of 4-week chicken), 0.84% in pancreas and 0.2% in small intestine.

EXAMPLE 4

Splicing Analysis of Chicken CCOL2A1 5' Propeptide Exon

Splicing analysis of the CCOL2A1 exon 2 in the tissue from chicken embryos was performed using RT-PCR. mRNA extracted from skin, liver, vitreum, cornea, pectoralis, small intestine, sternum, arthrodial cartilage and etc., and col2a1-5 and col2a1-5R sense and antisense primers listed in Table 1 were used for RT-PCR analysis. The specificity of the PCR products was determined by 1% agarose gel electrophoresis. The results of RT-PCR showed that exon 2 of chicken CCOL2A1 5' N propeptide was spliced and transcribed in heart, liver vitreum, cornea, pectoralis and small intestine, but not in cartilaginous tissue such as sternum and arthrodial cartilage (FIG. 6).

EXAMPLE 5

Mapping Chicken CCOL2A1 Gene Chromosomes

In order to precisely map map CCOL2A1 to the chromosome, using in situ hybridization (ISH) and DIG-High Prime DNA Labeling and Detection Starter Kit II (Roche), the gene fragments of the 3'-UTR chicken CCOL2A1 gene were labeled by digoxin as probes, and hybridized with the metaphase chromosome to map the chromosomes. After statistical analysis, the chicken CCOL2A1 gene was located to chromosome 4p2 (FIGS. 7, 8 and 9).

EXAMPLE 6

Chicken CCOL2A1 Homological Comparison

The homology of the cDNA and amino acid sequence of the type II collagen triple helix-forming region of the chicken CCOL2A1 was compared with that of various species such as dog (AF023169, AF242201), human (M M001844), zebrafish (U23822), and mouse (M65161) searched from GenBank using DNASTAR Megalign software (DNASTAR, Inc.). A phylogenetic tree was drawn using the Genedoc program (FIG. 10).

The results indicate that the amino acid and cDNA sequence of chicken CCOL2A 1 had 79.03% and 94.77% homology respectively with dog CII suggesting the highest homology in phylogeny; the next was between chicken and human, showing 78.96% and 93.89% identity. The homology between human and dog showed the highest identity among these five species, showing 91.89% identity of amino acid and 98.52% identity of cDNA, the next was between human and mouse, showing 88.63% and 96.15% identity respectively. A phylogenetic tree was constructed to represent the comparison results and analyze the homology.

EXAMPLE 7

Expression of Recombinant CCOL2A1 cDNA

The materials, reagents and instruments used in this experiment are described below:

The expression vectors pPIC9K, pPIC9, pPICZαA, B, C and yeast strains *Pichia pastoris* GS 115 and X33, Spheroplast kit for yeast and *Pichia* EasyComp™ were purchased from Invitrogen; Mung bean nuclease was from NEB; Mini protein 2 electrophoresis system and semi-dry electrophoretic transfer were from Bio-Rad; Gel-Pro image analyser system V3.1 was from Media Cybemetic; DU640 nucleic acid and protein analyzer was from Beckman.

1) The construction of the eukaryotic expression vector pPIC-ZaB/ CCOL2A1

The eukaryotic expression vector was constructed as follows: PCR was performed using the primers (sequence 25 5'GGT ACC TTG GTG GAA ACT TTG CGG 3'; SEQ ID No.18) and (sequence 26 5'GGT ACC GTT ACA AGA AGC AGA CTG 3'; SEQ ID No.19), and pGEM-T/CCOL2A1 as template. The PCR mixture contained 25 µl of 2×GC Buffer I, 4 µl of dNTP (2.5 mM), 0.5 µl of 20 µM primers. The PCR condition was after 96° C. at 5 min, then 4 cycles at 96° C. for 1 min, 6° C. for 1 min, 72° C. for 3 min and 26 cycles at 96° C. for 1 min, 65° C. for 30 s, 72° C. for 2.5 min and a final extension 72° C. for 5 min. The recovered PCR products were inserted into a pPICZαB expression vector, followed by a determination of the correct direction of inserts in expression vector pPICZαB/CCOL2A1 by BamHI digestion.

2) Construction of Yeast Expression Vector pPIC9K/CCOL2A1

In order to improve the stability and quantity of expression of the pPICZαB/CCOL2A1 vector in yeast P. pastoris, the CCOL2A1 fragment was inserted into the high copy vector pPIC9K, resulting in pPIC9K/CCOL2A1. The construction procedure is shown in Figure below. Briefly, pPICZαB/CCOL2A1 was linearized by digestion with Kpn I then digested by mung bean nuclease to generate blunt-ends. Simultaneously, pPIC9K was digested by the blunt-end enzyme SnaBI. The two fragments were ligated by T4 DNA ligase, resulting in an expression vector pPIC9K/CCOL2A1, and open reading frames were confirmed by sequencing 3) P. pastoris GS115 Preparation Protoplast Transformation Method The yeasts were transformed using the protoplast method:

a) P. pastoris GS 115 was spread on YPD plates by streak inoculation, followed by incubation at 30° C. for 2 d, inoculation of selected colonies in 5 ml of YPD medium, and incubation at 30° C. with agitation at 300 rpm overnight b) The cell suspensions with 1:1000 dilution was inoculated in 100 ml of YPD, incubated at 30° C. and agitated at 300 rpm until OD600 reached 0.2-0.3, followed by centrifuging at 1,500×g for 5 min and discharging the supernatant.

c) The cells were washed once with 20 ml sterilized water, 20 ml SED and 20 ml IM sorbitol, followed by centrifugation at 1500×g for 5 min. The supernatant was discarded after each wash. The cells were resuspended in 20 ml of SED, and divided 10 ml each into A and B tubes.

d) 800 µl of 15% SDS was added to each 1.5 ml eppendorf tube labeled 0, 2, 4, 5, 6, 8, 9, 10, 15, 18, 20, 25, 30, 35, 40, representing the time in the Zymolyase digesting cell well (min). 200 µl cells suspensions were taken from the A tube and frozen for the control of Zymolyase digesting time. 7.5 µl of Zymolyase (2.25 units) was added to the A tube, mixed slightly and maintained at 30° C. 200 µl of digested cells were taken from the A tube at each time according to the label and mixed with 800 µl of 5% SDS in eppendorf tubes, and placed on ice to stop the enzyme reaction.

e) The percentage of protoplast forming at each time point was calculated using the following equation: protoplast %=100−[(OD800 (min)/OD800 (0 min)×100). This equation was used to calculate the time (t, min) at which 70% of the protoplast was formed. 7.5 µl of Zymolyase was added to the B tube, and maintained at 30° C. for t time.

f) The protoplasts were centrifuged at 750×g for 10 min. Supernatants were discarded, and protoplasts were washed with 10 ml of 1 M of sorbitol and 10 ml of CaS respectively, supernatant was discarded, and the protoplasts were resuspended with 0.6 ml of CaS for transformation.

4) pPIC9K/CCOL2A1 and pPICZαB/CCOL2A1 Transformed GS115 Protoplast a) Approximately 10 µg of linearized pPICZαB/CCOL2A1 and pPIC9K/CCOL2A1 were mixed gently with 100 µl of freshly prepared protoplast followed by incubation at room temperature for 10 min. pPIC9K/GS 115 and pPIC-ZαB/GS11 blank vectors were used as negative controls.

b) One ml of freshly made PEG/CaT (1:1) solution was added and mixed gently followed by incubation at room temperature for 10 min.

c) Samples were centrifuged at 750×g for 10 min and as much of the supernatant as possible was removed. Cells were resuspended in 150 µl of SOS and incubated for 20 min, after which 850 µl of 1 M sorbitol was added.

d) Each 150 µl of transformed protoplasts were mixed with 10 ml of RD agar medium, spread on upper RDB plate, incubated at 28-30° C. for 4-6 d, after which the results were obtained.

5) pPICZαB/CCOL2A1/GS115 and pPIC9K/CCOL2A1/GS115 Positive Transformant Screening Cultured pPIC9K/CCOL2A1/GS115 and pPICZαB/CCOL2A1/GS115 grew approximately 100 transformants on RDB plates. In order to obtain a high copy number, each transformant was transferred to a plate containing various concentration of G418 or Zeocin (0418 concentration: 0.25 mg/ml, 0.5 mg/ml, 1 mg/ml, 2.0 mg/ml, 3.0 mg/ml, 4.0 mg/ml; Zeocin concentration: 100 µg/ml, 200 µg/ml) to screen for high copy number.

6) Extraction of the Yeast Genomic DNA, and Identification of the Integrated Target Gene in the Yeast Genome by PCR Resistant transformants and blank vectors were inoculated into 2 ml of YPD and cultured at 30° C. and shaken at 300 rpm for 2 d. The genomic DNA was extracted and inserts were detected by PCR using CCOL2A1 cDNA as specific primers: F:5'GGTACC TTG GTG GAA ACT TTG CGG 3', R: 5'GGTACC GTT ACA AGA AGC AGA CTG 3'. PCR conditions were 96° C. for 5 min, then 5 cycles at 96° C. for 1 min, 60° C. for 2 min, 72° C. for 3 min, and 25 cycles of 96° C. for 1 min, 58° C. for 1 min, 72° C. for 2 min, and a final extension at 72° C. for 5 min.

7) pPICZαB/CCOL2A1/GS115 and pPIC9K/CCOL2A1/GS115 Methanol-Induced Expression and Western Blot Analysis Positively-identified colonies were inoculated in 30 ml of BMGY medium and incubated at 28° C. and shaken at 300 rpm for 2 d. The cells were collected by centrifugation and resuspended with 1/10 volume of BMMY followed by further incubation at 28° C. and shaken at 300 rpm. Methanol was added to 1% of volume at 24-h intervals. The supernatant and yeast were harvested from the medium induced for 4 d. The supernatant was dialyzed, desalinated and lyophilized. The cell lysates from yeast were prepared by vortexing with ¼ volume of glass beads followed by collection via centrifugation. The induced cell lysates and supernatants were separated by 10% SDS-PAGE electrophoresis and transferred to nitrocellulose filters. The filters were blocked with 20% FBS at 4° C. overnight, incubated with a monoclonal antibody to 95D1A (1:1000) at room temperature for 2 h, and washed 3 times with TTBS, each 5 min. Filters were incubated with goat anti-mouse AP conjugated 2° C. antibody at room temperature for 2 h, and were washed again as described above. The signal was detected using a NBT/BCIP Reagent Kit Results:

The supernatant from each induced expression vector described above was desalinated, concentrated and identified by 10% SDS-PAGE electrophoresis and Western blot analysis. The results reveal that an 80 KD band representing the CCOL2A1α chain was only in the cytoplasm of the pPICZαB/CCOL2A1 transformant (FIG. 11A); however complete expression of the CCOL2A1α chain was detected in the cytoplasm of pPIC9K/CCOL2A (FIG. 11B), but not in the supernatant by western blot analysis.

EXAMPLE 8

Construction of prolyl 4-hydroxylase α and/or β Subunit

1) Prolyl 4-Hydroxylase α Subunit (P4Hα) cDNA Cloning

According to the chicken P4Hα gene sequence, primer a: 5'AGA TAC TGC TAC GAA AGA CCC CGA G 3' (SEQ ID No.20) and b: 5' CTC TCT TGG TTG TAG CCC TCA TCT G 3' (SEQ ID No.21) were designed. The PCR system contained 5 μl of 10×PCR Buffer, 5 μl of 25 mM $MgCl_2$, 4 μl of 2.5 mM dNTP Mix, 0.5 μl of 20 μM primers, 1 μl of cDNA, 0.5 μl Taq, and water to a final volume of 50 μl. PCR products were examined by 1% agarose electrophoresis. PCR conditions were 96° C. for 5 min, then 4 cycles of 96° C. for 1 min, 72° C. for 3 min and 26 cycles at 96° C. for 1 min, 69° C. for 1 min, 72° C. for 2 min and a final extension at 72° C. for 3 min.

2) Construction of the pPIC9K/P4Hα Eukaryotic Expression Vector

The P4Hα PCR product described above was ligated with pGEM-T, resulting in a pGEM-T/P4Hα plasmid. A Not I restriction site was introduced by PCR. The primers a: 5'GCG GCC GCA GAT ACT GCT ACG AAA G 3' (SEQ ID No.22) and b: 5'GCG GCC GCC TCT CTT GGT TGT AGG 3' (SEQ ID No.23), and Pfu DNA polymerase were used for PCR. PCR products were given polyA tails then ligated with a pGEM-T vector and sequenced. The target fragments were recovered after the pGEM-T/P4Hα was digested by Not I. The P4Hα gene fragment was ligated with the pPIC9K vector linearized by Not I using T4 DNA ligase resulting in a pPIC9KJP4Hα expression vector. The direction of insert was identified.

3) P4Hβ cDNA cloing and recombinant expression vector construction

According to the known chicken P4Hβ subunit gene sequence, the primers F:5'GCG GCC GCA CAG CCC CTG GAG GAG 3' (SEQ ID No.24) and R: 5'GCG GCC GCG GTG ATG TAG ATC AGT C 3' (SEQ ID No.25) were designed and Not I restriction sites were introduced. RNA was extracted from sternum of 17-day-old chicken embryos followed by RT-PCR. 1.5 mM $[Mg^{2+}]$ was used in the PCR system. PCR conditions were 96° C. for 5 min, then 4 cycles of 96° C. for 1 min, 53° C. for 1 min, 72° C. for 2 min and 26 cycles at 96° C. for 30 s, 51° C. for 30 s, 72° C. for 2 min and a final extension at 72° C. for 5 min. The PCR products were inserted into a pGEM-T for sequencing. The colonies with the correct sequence were inserted into a pPIC9 expression vector, resulting in the pPIC9/P4H P expression vector.

EXAMPLE 9

Coexpression of pPIC9K/P4Hα, pPIC9/P4Hβ and pPICZαB/CCOL2A1 in Yeast GS115

The expression vectors pPIC9K/P4Hα, pPIC9/P4Hβ and pPICZαB/CCOL2A1 described in Examples 7 and 8 were linearized by Bgl II, Sal I and Pmel I. 10 μg of linearized vector was transformed into GS115. The transformants were cultured on MM plates containing G418 and Zeocin at 30° C. for 4-6 d.

EXAMPLE 10

Construction of Double Expression Vector pPICZαA/P4Hα-β

During co-expression of pPIC9K/P4Hα, pPIC9/P4Hβ and pPICZαB/CCOL2A1, the positive clones were unstable. In order to overcome the deficiency of the construction described above, P4Hα and P4H β were constructed into the same expression vector pPICZαA, resulting in a pPICZαA/P4Hα-P4Hβ double expression vector.

PCR was performed using the plasmids pGEM-T/P4Hα and pGEM-T/P4Hβ in Example 8 and 9, as templates. The primers' sequences were P4Hα: F: 5'GCGGCCGC GAT ACT GCT ACG AAA G3' (SEQ ID No.26); R: 5'GCGGCCGC CTC CAA CTC TGA TAA C 3' (SEQ ID No.27); P4Hβ : F: 5'GCGGCCGC CAG CCC CTG GAG GAG -3 (SEQ ID No.28)'; and R: 5' GCGGCCGC TTA ATC ATC ATC AGC 3' (SEQ ID No.29). PCR conditions were 96° C. for 5 min, then 4 cycles at 96° C. for 1 min, 66° C. for 80 s, 72° C. for 90 s and 26 cycles at 96° C. for 1 min, 64° C. for 40 s, 72° C. for 50 s and a final extension at 72° C. for 5 min. PCR products were examined by 1% agarose gel electrophoresis. The specific target fragments were recovered and inserted into pGEM-Teasy followed by sequencing.

pGEM-T/P4Hα and pGEM-T/P4Hβ confirmed by sequencing were digested by Not I, ligated with pPICZαA, resulting in recombinant expression vectors pPICZαA/P4Hα and pPICZαA/P4Hβ.

A P4Hβ full-expression unit was cut from pPICZαA/P4Hβ, and inserted into pPICZαA/P4Hα. Since Bgl II and Bam HI are isoschizomers, these sites can link with linearized pPICZαA/P4Hα by Bgl II resulting in the double expression vector pPICZαA/P4Hα-β.

Since the P4Hβ expression unit was located upstream, PCR was used to examine whether the direction of P4Hα and βwas coincident. The upstream primer (5' GCGGCCGC CAG CCC CTG GAG GAG 3') (SEQ ID No.28) and downstream primer (5' GCGGCCGC CTC CAA CTC TGA TAA C 3') (SEQ ID No.27) for amplifying P4Hα was used to PCR. If the directions of inserts were correct, 4644bp PCR products would be apparent, otherwise, there would be no expression band.

EXAMPLE 11

Co-Expression of pPIC9K/CCOL2A1 and pPICZαA/P4Hα-β pPIC9K/CCOL2A1 and pPICZαA/P4Hα-β were co-transformed into GS115 to study expression of the three genes. Protoplast preparation, positive transformant screening, PCR identifying and methanol induction were performed as described above.

The induced pPICZ(B/CCOL2A1/GS115 and pPIC9K/P4H) co-expression products in supernatants and cytolysates were identified by SDS-PAGE and Western blot analysis. FIG. 12 showed shows that the full-length of CCOL2A1 (chain was only expressed in the cytolysate, but not in the supernatants.

The invention claimed is:
1. An isolated polynucleotide, comprising SEQ ID NO: 2.
2. A recombinant expression vector comprising the isolated polynucleotide of claim or 1.
3. A host cell transformed with the recombinant expression vector of claim 2.
4. A method for producing a recombinant polypeptide, comprising transforming a suitable host cell by the recombinant expression vector of claim 3;

culturing the host cell in suitable culture medium and under appropriate culture conditions; and separating and purifying the recombinant polypeptide from the culture medium, the cells, or the medium and the cells.

* * * * *